(12) United States Patent
Iannotti et al.

(10) Patent No.: US 10,973,535 B2
(45) Date of Patent: Apr. 13, 2021

(54) SYSTEM OF PREOPERATIVE PLANNING AND PROVISION OF PATIENT-SPECIFIC SURGICAL AIDS

(71) Applicant: THE CLEVELAND CLINIC FOUNDATION, Cleveland, OH (US)

(72) Inventors: Joseph P. Iannotti, Strongsville, OH (US); Wael K. Barsoum, Bay Village, OH (US); Jason A. Bryan, Avon Lake, OH (US); Peter D. O'Neill, Shaker Heights, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 602 days.

(21) Appl. No.: 15/642,424

(22) Filed: Jul. 6, 2017

(65) Prior Publication Data
US 2017/0296205 A1    Oct. 19, 2017

Related U.S. Application Data

(63) Continuation of application No. 13/282,550, filed on Oct. 27, 2011, now Pat. No. 9,717,508.
(Continued)

(51) Int. Cl.
*A61B 17/17* (2006.01)
*A61B 34/10* (2016.01)
(Continued)

(52) U.S. Cl.
CPC .......... *A61B 17/1739* (2013.01); *A61B 34/10* (2016.02); *A61B 17/1778* (2016.11);
(Continued)

(58) Field of Classification Search
CPC ............................ A61B 17/1739; A61B 34/10
(Continued)

(56) References Cited

U.S. PATENT DOCUMENTS

| 4,841,975 A | 6/1989 | Woolson |
| 4,976,737 A | 12/1990 | Leake |

(Continued)

FOREIGN PATENT DOCUMENTS

| AU | 2004293091 A1 | 6/2005 |
| AU | 2004293104 A1 | 6/2005 |

(Continued)

OTHER PUBLICATIONS

Audenaert et al. ("A custom-made guide for femoral component positioning in hip resurfacing arthroplasty: development and validation study", Informa UK Ltd, 2011, pp. 304-309) (Year: 2011).*
(Continued)

*Primary Examiner* — Iftekhar A Khan
(74) *Attorney, Agent, or Firm* — Norton Rose Fulbright Canada LLP

(57) ABSTRACT

A method of preoperative planning comprises creating a virtual model of a native patient tissue; placing a virtual device into a desired device orientation relative to the virtual model of the native patient tissue; specifying at least one structural change to the native patient tissue to facilitate placement of the virtual device in the desired device orientation; creating a virtual model of an altered patient tissue responsive to the specifying at least one structural change to the native patient tissue; and fabricating a tangible representation of a bone using the virtual model of the altered patient tissue.

19 Claims, 16 Drawing Sheets

Related U.S. Application Data

(60) Provisional application No. 61/408,392, filed on Oct. 29, 2010.

(51) Int. Cl.
*A61B 17/56* (2006.01)
*A61F 2/40* (2006.01)
*A61F 2/46* (2006.01)
*A61B 34/00* (2016.01)

(52) U.S. Cl.
CPC ......... *A61B 34/25* (2016.02); *A61B 2017/568* (2013.01); *A61B 2034/105* (2016.02); *A61B 2034/108* (2016.02); *A61F 2/4081* (2013.01); *A61F 2002/4633* (2013.01)

(58) Field of Classification Search
USPC .......................................................... 703/1
See application file for complete search history.

(56) References Cited

U.S. PATENT DOCUMENTS

| | | | |
|---|---|---|---|
| 5,098,383 A * | 3/1992 | Hemmy | A61B 17/17 604/116 |
| 5,250,050 A * | 10/1993 | Poggie | A61B 17/154 606/79 |
| 5,490,854 A | 2/1996 | Fisher et al. | |
| 5,682,886 A | 11/1997 | Delp et al. | |
| 5,768,134 A | 6/1998 | Swaelens et al. | |
| 5,871,018 A | 2/1999 | Delp et al. | |
| 5,916,219 A | 6/1999 | Matsuno et al. | |
| 6,205,411 B1 | 3/2001 | DiGioia, III et al. | |
| 6,327,491 B1 * | 12/2001 | Franklin | A61B 90/11 600/429 |
| 6,711,432 B1 | 3/2004 | Krause et al. | |
| 6,772,026 B2 | 8/2004 | Bradbury et al. | |
| 7,194,120 B2 | 3/2007 | Wicker et al. | |
| 7,357,057 B2 | 4/2008 | Chiang | |
| 7,468,075 B2 | 12/2008 | Lang et al. | |
| 7,510,557 B1 | 3/2009 | Bonutti | |
| 7,534,263 B2 * | 5/2009 | Burdulis, Jr. | A61B 17/155 606/88 |
| 7,618,451 B2 | 11/2009 | Berez et al. | |
| 7,634,119 B2 | 12/2009 | Tsougarakis et al. | |
| 7,717,956 B2 | 5/2010 | Lang | |
| 7,792,249 B2 * | 9/2010 | Gertner | A61F 9/008 378/65 |
| 7,796,791 B2 | 9/2010 | Tsougarakis et al. | |
| 7,799,077 B2 | 9/2010 | Lang et al. | |
| 7,806,896 B1 | 10/2010 | Bonutti | |
| 7,806,897 B1 | 10/2010 | Bonutti | |
| 7,967,868 B2 | 6/2011 | White et al. | |
| 7,981,158 B2 * | 7/2011 | Fitz | A61F 2/38 623/17.16 |
| 8,062,302 B2 | 11/2011 | Lang et al. | |
| 8,066,708 B2 | 11/2011 | Lang et al. | |
| 8,070,752 B2 | 12/2011 | Metzger et al. | |
| 8,077,950 B2 | 12/2011 | Tsougarakis et al. | |
| 8,083,745 B2 | 12/2011 | Lang et al. | |
| 8,092,465 B2 * | 1/2012 | Metzger | A61B 17/56 606/96 |
| 8,094,900 B2 | 1/2012 | Steines et al. | |
| 8,105,330 B2 | 1/2012 | Fitz et al. | |
| 8,122,582 B2 | 2/2012 | Burdulis, Jr. et al. | |
| 8,133,234 B2 | 3/2012 | Meridew et al. | |
| 8,160,345 B2 | 4/2012 | Pavlovskaia et al. | |
| 8,175,683 B2 | 5/2012 | Roose | |
| 8,221,430 B2 | 7/2012 | Park et al. | |
| 8,234,097 B2 | 7/2012 | Steines et al. | |
| 8,241,293 B2 | 8/2012 | Stone et al. | |
| 8,282,646 B2 | 10/2012 | Schoenefeld et al. | |
| 8,298,237 B2 | 10/2012 | Schoenefeld | |
| 8,337,501 B2 | 12/2012 | Fitz et al. | |
| 8,337,507 B2 | 12/2012 | Lang et al. | |
| 8,343,218 B2 | 1/2013 | Lang et al. | |
| 8,366,771 B2 | 2/2013 | Burdulis et al. | |
| 8,377,129 B2 | 2/2013 | Fitz et al. | |
| 8,439,926 B2 | 5/2013 | Bojarski et al. | |
| 8,460,304 B2 | 6/2013 | Fitz et al. | |
| 8,480,754 B2 * | 7/2013 | Bojarski | A61B 17/155 623/20.35 |
| 8,500,740 B2 | 8/2013 | Bojarski et al. | |
| 8,529,568 B2 | 9/2013 | Bouadi | |
| 8,529,630 B2 | 9/2013 | Bojarski | |
| 8,585,708 B2 | 9/2013 | Fitz et al. | |
| 8,545,569 B2 | 10/2013 | Fitz et al. | |
| 8,551,099 B2 | 10/2013 | Lang | |
| 8,551,102 B2 | 10/2013 | Fitz et al. | |
| 8,551,103 B2 | 10/2013 | Fitz et al. | |
| 8,551,169 B2 | 10/2013 | Fitz et al. | |
| 8,556,906 B2 | 10/2013 | Fitz et al. | |
| 8,556,907 B2 | 10/2013 | Fitz et al. | |
| 8,556,971 B2 | 10/2013 | Lang | |
| 8,556,983 B2 * | 10/2013 | Bojarski | A61F 2/3859 623/20.35 |
| 8,561,278 B2 | 10/2013 | Fitz et al. | |
| 8,562,611 B2 | 10/2013 | Fitz et al. | |
| 8,562,618 B2 | 10/2013 | Fitz et al. | |
| 8,568,479 B2 | 10/2013 | Fitz et al. | |
| 8,568,480 B2 | 10/2013 | Fitz et al. | |
| 8,617,172 B2 | 12/2013 | Fitz et al. | |
| 8,617,242 B2 | 12/2013 | Philipp | |
| 8,623,026 B2 | 1/2014 | Wong et al. | |
| 8,634,617 B2 | 1/2014 | Tsougarakis et al. | |
| 8,638,998 B2 | 1/2014 | Steines et al. | |
| 8,641,716 B2 | 2/2014 | Fitz et al. | |
| 8,657,827 B2 | 2/2014 | Fitz et al. | |
| 8,682,052 B2 | 3/2014 | Fitz et al. | |
| 8,728,168 B2 * | 5/2014 | Hanssen | A61F 2/36 623/22.24 |
| 8,771,365 B2 * | 7/2014 | Bojarski | A61F 2/3886 623/20.32 |
| 2003/0055502 A1 | 3/2003 | Lang et al. | |
| 2003/0176860 A1 * | 9/2003 | Shimura | A61B 34/10 606/53 |
| 2003/0216669 A1 | 11/2003 | Lang et al. | |
| 2004/0068187 A1 | 4/2004 | Krause et al. | |
| 2004/0133276 A1 | 7/2004 | Lang et al. | |
| 2004/0138754 A1 | 7/2004 | Lang et al. | |
| 2004/0147927 A1 | 7/2004 | Tsougarakis et al. | |
| 2004/0153079 A1 | 8/2004 | Tsougarakis et al. | |
| 2004/0204644 A1 | 10/2004 | Tsougarakis et al. | |
| 2004/0204760 A1 | 10/2004 | Fitz et al. | |
| 2004/0236424 A1 | 11/2004 | Berez et al. | |
| 2005/0148843 A1 | 7/2005 | Roose | |
| 2005/0234461 A1 | 10/2005 | Burdulis et al. | |
| 2005/0267584 A1 | 12/2005 | Burdulis et al. | |
| 2006/0111722 A1 | 5/2006 | Bouadi | |
| 2007/0083266 A1 | 4/2007 | Lang | |
| 2007/0100346 A1 * | 5/2007 | Wyss | A61B 17/17 606/87 |
| 2007/0100462 A1 | 5/2007 | Lang et al. | |
| 2007/0156171 A1 | 7/2007 | Lang et al. | |
| 2007/0157783 A1 | 7/2007 | Chiang | |
| 2007/0173815 A1 | 7/2007 | Murase | |
| 2007/0198022 A1 * | 8/2007 | Lang | A61F 2/38 606/88 |
| 2007/0226986 A1 | 10/2007 | Park et al. | |
| 2007/0233141 A1 | 10/2007 | Park et al. | |
| 2007/0233269 A1 | 10/2007 | Steines et al. | |
| 2007/0250169 A1 | 10/2007 | Lang | |
| 2007/0288030 A1 | 12/2007 | Metzger et al. | |
| 2008/0114370 A1 | 5/2008 | Schoenefeld | |
| 2008/0147072 A1 | 6/2008 | Park et al. | |
| 2008/0161815 A1 * | 7/2008 | Schoenefeld | A61B 17/1764 606/87 |
| 2008/0195216 A1 | 8/2008 | Philipp | |
| 2008/0208200 A1 * | 8/2008 | Crofford | A61B 17/175 606/88 |
| 2008/0243127 A1 * | 10/2008 | Lang | A61B 17/155 606/87 |
| 2008/0269906 A1 | 10/2008 | Iannotti et al. | |

(56) References Cited

U.S. PATENT DOCUMENTS

| | | |
|---|---|---|
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287954 A1* | 11/2008 | Kunz ............... A61B 17/175 606/87 |
| 2009/0018546 A1* | 1/2009 | Daley ............... A61B 17/175 606/92 |
| 2009/0024131 A1 | 1/2009 | Metzgu et al. |
| 2009/0087276 A1* | 4/2009 | Rose ............... A61B 17/155 409/79 |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0093816 A1 | 4/2009 | Roose et al. |
| 2009/0099567 A1 | 4/2009 | Zajac |
| 2009/0110498 A1 | 4/2009 | Park et al. |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0157083 A1 | 6/2009 | Park et al. |
| 2009/0163922 A1 | 6/2009 | Meridew et al. |
| 2009/0222014 A1* | 9/2009 | Bojarski ............ A61B 17/1767 606/88 |
| 2009/0222016 A1* | 9/2009 | Park ................. A61F 2/3609 606/89 |
| 2009/0222103 A1 | 9/2009 | Fitz et al. |
| 2009/0226068 A1 | 9/2009 | Fitz et al. |
| 2009/0228113 A1 | 9/2009 | Lang et al. |
| 2009/0254093 A1* | 10/2009 | White ............... A61B 17/175 606/89 |
| 2009/0270868 A1 | 10/2009 | Park et al. |
| 2009/0276045 A1 | 11/2009 | Lang |
| 2009/0306676 A1 | 12/2009 | Lang et al. |
| 2009/0307893 A1 | 12/2009 | Burdulis, Jr. et al. |
| 2009/0312805 A1 | 12/2009 | Lang et al. |
| 2010/0023015 A1 | 1/2010 | Park |
| 2010/0042105 A1 | 2/2010 | Park et al. |
| 2010/0049195 A1 | 2/2010 | Park et al. |
| 2010/0054572 A1 | 3/2010 | Tsougarakis et al. |
| 2010/0082035 A1 | 4/2010 | Keefer |
| 2010/0087829 A1 | 4/2010 | Metzger et al. |
| 2010/0152741 A1 | 6/2010 | Park et al. |
| 2010/0152782 A1 | 6/2010 | Stone et al. |
| 2010/0160917 A1 | 6/2010 | Fitz et al. |
| 2010/0168754 A1 | 7/2010 | Fitz et al. |
| 2010/0174376 A1 | 7/2010 | Lang et al. |
| 2010/0185202 A1 | 7/2010 | Lester et al. |
| 2010/0191244 A1 | 7/2010 | White et al. |
| 2010/0212138 A1 | 8/2010 | Carroll et al. |
| 2010/0217270 A1 | 8/2010 | Polinski et al. |
| 2010/0217338 A1 | 8/2010 | Carroll et al. |
| 2010/0228257 A1 | 9/2010 | Bonutti |
| 2010/0234849 A1 | 9/2010 | Bouadi |
| 2010/0256479 A1 | 10/2010 | Park et al. |
| 2010/0262150 A1 | 10/2010 | Lian |
| 2010/0274534 A1 | 10/2010 | Steines et al. |
| 2010/0281678 A1 | 11/2010 | Burdulis, Jr. et al. |
| 2010/0286700 A1 | 11/2010 | Snider et al. |
| 2010/0298894 A1 | 11/2010 | Bojarski et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305573 A1 | 12/2010 | Fitz et al. |
| 2010/0305574 A1 | 12/2010 | Fitz et al. |
| 2010/0305708 A1 | 12/2010 | Lang et al. |
| 2010/0305907 A1 | 12/2010 | Fitz et al. |
| 2010/0329530 A1 | 12/2010 | Lang et al. |
| 2011/0015636 A1 | 1/2011 | Katrana et al. |
| 2011/0015637 A1 | 1/2011 | De Smedt et al. |
| 2011/0015639 A1 | 1/2011 | Metzger et al. |
| 2011/0029091 A1 | 2/2011 | Bojarski et al. |
| 2011/0029093 A1 | 2/2011 | Bojarski et al. |
| 2011/0040168 A1 | 2/2011 | Arnaud et al. |
| 2011/0040303 A1 | 2/2011 | Iannotti |
| 2011/0054478 A1 | 3/2011 | Vanasse et al. |
| 2011/0060341 A1 | 3/2011 | Angibaud et al. |
| 2011/0066193 A1 | 3/2011 | Lang et al. |
| 2011/0066245 A1 | 3/2011 | Lang et al. |
| 2011/0066252 A1 | 3/2011 | Hanssen |
| 2011/0071533 A1 | 3/2011 | Metzger et al. |
| 2011/0071581 A1 | 3/2011 | Lang et al. |
| 2011/0071645 A1 | 3/2011 | Bojarski et al. |
| 2011/0071802 A1 | 3/2011 | Bojarski et al. |
| 2011/0087332 A1* | 4/2011 | Bojarski ............ A61B 17/1764 623/20.32 |
| 2011/0092977 A1 | 4/2011 | Salehi et al. |
| 2011/0093108 A1 | 4/2011 | Ashby et al. |
| 2011/0106093 A1 | 5/2011 | Romano et al. |
| 2011/0144760 A1 | 6/2011 | Wong et al. |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0184419 A1 | 7/2011 | Meridew et al. |
| 2011/0190775 A1 | 8/2011 | Ure |
| 2011/0196377 A1 | 8/2011 | Hodorek et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213376 A1 | 9/2011 | Maxson et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0214279 A1 | 9/2011 | Park et al. |
| 2011/0218539 A1 | 9/2011 | Fitz et al. |
| 2011/0218545 A1 | 9/2011 | Catanzarite et al. |
| 2011/0218584 A1 | 9/2011 | Fitz et al. |
| 2011/0224674 A1 | 9/2011 | White et al. |
| 2011/0230888 A1 | 9/2011 | Lang et al. |
| 2011/0238073 A1 | 9/2011 | Lang et al. |
| 2011/0245835 A1 | 10/2011 | Dodds et al. |
| 2011/0266265 A1 | 11/2011 | Lang |
| 2011/0295329 A1 | 12/2011 | Fitz et al. |
| 2011/0295378 A1* | 12/2011 | Bojarski ............ A61F 2/30 623/20.35 |
| 2011/0313423 A1 | 12/2011 | Lang et al. |
| 2011/0313424 A1 | 12/2011 | Bono et al. |
| 2011/0319897 A1 | 12/2011 | Lang et al. |
| 2011/0319900 A1 | 12/2011 | Lang et al. |
| 2012/0010711 A1 | 1/2012 | Antonyshyn et al. |
| 2012/0029520 A1 | 2/2012 | Lang et al. |
| 2012/0041445 A1 | 2/2012 | Roose et al. |
| 2012/0041446 A1 | 2/2012 | Wong et al. |
| 2012/0065640 A1 | 3/2012 | Metzger et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0078254 A1 | 3/2012 | Ashby et al. |
| 2012/0078258 A1 | 3/2012 | Lo et al. |
| 2012/0078259 A1 | 3/2012 | Meridew |
| 2012/0093377 A1 | 4/2012 | Tsougarakis et al. |
| 2012/0101503 A1 | 4/2012 | Lang et al. |
| 2012/0109138 A1 | 5/2012 | Meridew et al. |
| 2012/0116203 A1 | 5/2012 | Vancraen et al. |
| 2012/0116562 A1 | 5/2012 | Agnihotri et al. |
| 2012/0123422 A1 | 5/2012 | Agnihotri et al. |
| 2012/0123423 A1 | 5/2012 | Fryman |
| 2012/0130382 A1* | 5/2012 | Iannotti ............. A61F 2/4607 606/87 |
| 2012/0130502 A1* | 5/2012 | Podolsky ........... A61F 2/34 623/22.4 |
| 2012/0130687 A1 | 5/2012 | Otto et al. |

(56) References Cited

U.S. PATENT DOCUMENTS

| | | |
|---|---|---|
| 2012/0141034 A1 | 6/2012 | Iannotti et al. |
| 2012/0143197 A1 | 6/2012 | Lang et al. |
| 2012/0143198 A1* | 6/2012 | Boyer .................. A61B 17/157 606/87 |
| 2012/0151730 A1 | 6/2012 | Fitz et al. |
| 2012/0158001 A1 | 6/2012 | Burdulis, Jr. et al. |
| 2012/0165820 A1 | 6/2012 | De Smedt et al. |
| 2012/0172884 A1 | 7/2012 | Zheng et al. |
| 2012/0191205 A1 | 7/2012 | Bojarski et al. |
| 2012/0191420 A1 | 7/2012 | Bojarski et al. |
| 2012/0192401 A1 | 8/2012 | Pavlovskaia et al. |
| 2012/0197260 A1 | 8/2012 | Fitz et al. |
| 2012/0197408 A1 | 8/2012 | Lang et al. |
| 2012/0201440 A1 | 8/2012 | Steines et al. |
| 2012/0209276 A1 | 8/2012 | Schuster |
| 2012/0209394 A1* | 8/2012 | Bojarski .............. A61B 17/157 623/20.32 |
| 2012/0215226 A1 | 8/2012 | Bonutti |
| 2012/0221008 A1 | 8/2012 | Carroll et al. |
| 2012/0226283 A1 | 9/2012 | Meridew et al. |
| 2012/0232669 A1 | 9/2012 | Bojarski et al. |
| 2012/0232670 A1 | 9/2012 | Bojarski et al. |
| 2012/0232671 A1 | 9/2012 | Bojarski |
| 2012/0239045 A1 | 9/2012 | Li |
| 2012/0245647 A1 | 9/2012 | Kunz et al. |
| 2012/0245699 A1 | 9/2012 | Lang et al. |
| 2012/0265208 A1 | 10/2012 | Smith |
| 2012/0265496 A1 | 10/2012 | Mahfouz |
| 2012/0271366 A1 | 10/2012 | Katrana et al. |
| 2012/0276509 A1* | 11/2012 | Iannotti ................ A61F 2/4081 434/267 |
| 2012/0277751 A1 | 11/2012 | Catanzarite et al. |
| 2012/0289966 A1 | 11/2012 | Fitz et al. |
| 2012/0290272 A1* | 11/2012 | Bryan .................. A61B 34/10 703/1 |
| 2012/0296337 A1 | 11/2012 | Fitz et al. |
| 2013/0018379 A1 | 1/2013 | Fitz et al. |
| 2013/0018380 A1 | 1/2013 | Fitz et al. |
| 2013/0018464 A1 | 1/2013 | Fitz et al. |
| 2013/0023884 A1 | 1/2013 | Fitz et al. |
| 2013/0024000 A1 | 1/2013 | Bojarski et al. |
| 2013/0030419 A1* | 1/2013 | Fitz ...................... A61B 17/15 606/1 |
| 2013/0030441 A1 | 1/2013 | Fitz et al. |
| 2013/0079781 A1 | 3/2013 | Fitz et al. |
| 2013/0079876 A1 | 3/2013 | Fitz et al. |
| 2013/0081247 A1 | 4/2013 | Fitz et al. |
| 2013/0096562 A1 | 4/2013 | Fitz et al. |
| 2013/0103363 A1 | 4/2013 | Lang et al. |
| 2013/0110471 A1 | 5/2013 | Lang et al. |
| 2013/0123792 A1 | 5/2013 | Fitz et al. |
| 2013/0184713 A1 | 7/2013 | Bojarski et al. |
| 2013/0197870 A1 | 8/2013 | Steines et al. |
| 2013/0211409 A1 | 8/2013 | Burdulis, Jr. et al. |
| 2013/0211410 A1 | 8/2013 | Landes et al. |
| 2013/0211531 A1* | 8/2013 | Steines ................ A61F 2/3859 623/20.35 |
| 2013/0245803 A1 | 9/2013 | Lang |
| 2013/0253522 A1 | 9/2013 | Bojarski et al. |
| 2013/0289570 A1 | 10/2013 | Chao |
| 2013/0296874 A1 | 11/2013 | Chao |
| 2013/0297031 A1 | 11/2013 | Hafez |
| 2013/0317511 A1 | 11/2013 | Bojarski et al. |
| 2013/0331850 A1 | 12/2013 | Bojarski et al. |
| 2014/0005792 A1 | 1/2014 | Lang et al. |
| 2014/0029814 A1 | 1/2014 | Fitz et al. |
| 2014/0031826 A1 | 1/2014 | Bojarski et al. |
| 2014/0039631 A1 | 2/2014 | Bojarski et al. |
| 2014/0058396 A1 | 2/2014 | Fitz et al. |
| 2014/0058397 A1 | 2/2014 | Fitz et al. |
| 2014/0066935 A1 | 3/2014 | Fitz et al. |
| 2014/0066936 A1 | 3/2014 | Fitz et al. |
| 2014/0074441 A1 | 3/2014 | Fitz et al. |
| 2014/0086780 A1 | 3/2014 | Miller et al. |
| 2014/0228860 A1* | 8/2014 | Steines ................ A61B 34/30 606/130 |
| 2014/0343403 A1* | 11/2014 | Kunz .................... A61B 90/06 600/424 |

FOREIGN PATENT DOCUMENTS

| | | |
|---|---|---|
| AU | 2005309692 A1 | 6/2006 |
| AU | 2005311558 A1 | 6/2006 |
| AU | 2002310193 B2 | 3/2007 |
| AU | 2006297137 A1 | 4/2007 |
| AU | 2002310193 B8 | 5/2007 |
| AU | 2007202573 A1 | 6/2007 |
| AU | 2007212033 A1 | 8/2007 |
| AU | 2007226924 A1 | 9/2007 |
| AU | 2009221773 A1 | 9/2009 |
| AU | 2009246474 A1 | 11/2009 |
| AU | 2010201200 A1 | 4/2010 |
| AU | 2011203237 A1 | 7/2011 |
| AU | 2010217903 A1 | 9/2011 |
| AU | 2010236263 A1 | 11/2011 |
| AU | 2010264466 A1 | 2/2012 |
| AU | 2010289706 A1 | 3/2012 |
| AU | 2010315099 A1 | 5/2012 |
| AU | 2010327987 A1 | 6/2012 |
| AU | 2011203237 B2 | 10/2012 |
| AU | 2012216829 A1 | 10/2012 |
| AU | 2012217654 A1 | 10/2013 |
| AU | 2007212033 B2 | 1/2014 |
| AU | 2014200073 A1 | 1/2014 |
| AU | 2012289973 A1 | 3/2014 |
| AU | 2012296556 A1 | 3/2014 |
| CA | 2501041 A1 | 4/2004 |
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2804883 A1 | 6/2005 |
| CA | 2588907 A1 | 6/2006 |
| CA | 2590534 A1 | 6/2006 |
| CA | 2623834 A1 | 4/2007 |
| CA | 2641241 A1 | 8/2007 |
| CA | 2646288 A1 | 9/2007 |
| CA | 2717760 A1 | 9/2009 |
| CA | 2765499 A1 | 12/2010 |
| CA | 2771573 A1 | 3/2011 |
| CA | 2779283 A1 | 5/2011 |
| CA | 2782137 A1 | 6/2011 |
| CA | 2546965 C | 3/2013 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 101384230 A | 3/2009 |
| CN | 101442960 A | 5/2009 |
| CN | 100502808 C | 6/2009 |
| CN | 102006841 A | 4/2011 |
| CN | 102125448 A | 7/2011 |
| CN | 102405032 A | 4/2012 |
| CN | 102448394 A | 5/2012 |
| CN | 101420911 B | 7/2012 |
| CN | 102599960 A | 7/2012 |
| CN | 1913844 B | 9/2012 |
| CN | 102711670 A | 10/2012 |
| CN | 102724934 A | 10/2012 |
| CN | 102805677 A | 12/2012 |
| CN | 1729483 B | 10/2013 |
| CN | 103476363 A | 12/2013 |
| DE | 60336002 D1 | 3/2011 |
| DE | 60239674 D1 | 5/2011 |
| DE | 602004032166 D1 | 5/2011 |
| DE | 602005027391 D1 | 5/2011 |
| EP | 0558789 A1 | 9/1993 |
| EP | 1555962 A1 | 7/2005 |
| EP | 1558181 A1 | 8/2005 |
| EP | 1567985 A2 | 8/2005 |

(56) References Cited

FOREIGN PATENT DOCUMENTS

| | | |
|---|---|---|
| EP | 1575460 A2 | 9/2005 |
| EP | 1686930 A1 | 8/2006 |
| EP | 1686931 A1 | 8/2006 |
| EP | 1389980 A4 | 4/2007 |
| EP | 1814491 A1 | 8/2007 |
| EP | 1833387 A1 | 9/2007 |
| EP | 1686930 A4 | 10/2007 |
| EP | 1686931 A4 | 1/2008 |
| EP | 1928359 A2 | 6/2008 |
| EP | 1951136 A1 | 8/2008 |
| EP | 1981409 A2 | 10/2008 |
| EP | 1996121 A2 | 12/2008 |
| EP | 2114312 A2 | 11/2009 |
| EP | 2124764 A1 | 12/2009 |
| EP | 2 168 507 A2 | 3/2010 |
| EP | 1928359 A4 | 10/2010 |
| EP | 2259753 A1 | 12/2010 |
| EP | 2265199 A1 | 12/2010 |
| EP | 1555962 B1 | 2/2011 |
| EP | 2292188 A2 | 3/2011 |
| EP | 2292189 A2 | 3/2011 |
| EP | 1389980 B1 | 4/2011 |
| EP | 1686930 B1 | 4/2011 |
| EP | 1833387 B1 | 4/2011 |
| EP | 2303193 A1 | 4/2011 |
| EP | 2316357 A1 | 5/2011 |
| EP | 2324799 A2 | 5/2011 |
| EP | 2335654 A1 | 6/2011 |
| EP | 2403434 A1 | 1/2012 |
| EP | 2405865 A2 | 1/2012 |
| EP | 2419035 A1 | 2/2012 |
| EP | 2265199 A4 | 3/2012 |
| EP | 2303193 A4 | 3/2012 |
| EP | 2259753 A4 | 4/2012 |
| EP | 2292188 A3 | 5/2012 |
| EP | 2292189 A3 | 5/2012 |
| EP | 2445451 A1 | 5/2012 |
| EP | 2470126 A1 | 7/2012 |
| EP | 2496183 A2 | 9/2012 |
| EP | 2509539 A2 | 10/2012 |
| EP | 2512381 A2 | 10/2012 |
| EP | 2324799 A3 | 1/2013 |
| EP | 2419035 A4 | 1/2013 |
| EP | 2445451 A4 | 3/2013 |
| EP | 2403434 A4 | 4/2013 |
| EP | 2591756 A1 | 5/2013 |
| EP | 2496183 A4 | 12/2013 |
| EP | 2512381 A4 | 12/2013 |
| EP | 2649951 A2 | 12/2013 |
| EP | 2649951 A3 | 12/2013 |
| EP | 2671520 A3 | 12/2013 |
| EP | 2671521 A3 | 12/2013 |
| EP | 2671522 A3 | 12/2013 |
| EP | 2114312 B1 | 1/2014 |
| EP | 2710967 A2 | 3/2014 |
| GB | 2484042 A | 3/2012 |
| GB | 2489884 A | 10/2012 |
| GB | 201213674 | 10/2012 |
| GB | 2484042 B | 3/2014 |
| HK | 1059882 A1 | 8/2011 |
| HK | 1072710 A1 | 8/2011 |
| HK | 1087324 A1 | 11/2011 |
| HK | 1104776 A1 | 11/2011 |
| JP | 2006510403 A | 3/2006 |
| JP | 2007514470 A | 6/2007 |
| JP | 2011519713 A | 7/2011 |
| JP | 2011224384 A | 11/2011 |
| JP | 2012091033 A | 5/2012 |
| JP | 2012176318 A | 9/2012 |
| JP | 5053515 B2 | 10/2012 |
| JP | 2012187415 A | 10/2012 |
| JP | 2012523897 A | 10/2012 |
| JP | 5074036 B2 | 11/2012 |
| JP | 2012531265 A | 12/2012 |
| JP | 2013503007 A | 1/2013 |
| JP | 5148284 B2 | 2/2013 |
| JP | 5198069 B2 | 5/2013 |
| JP | 2014000425 A | 1/2014 |
| KR | 20050072500 A | 7/2005 |
| KR | 20050084024 A | 8/2005 |
| KR | 20120090997 A | 8/2012 |
| KR | 20120102576 A | 9/2012 |
| MX | 2012007140 A | 1/2013 |
| NZ | 597261 A | 11/2013 |
| SG | 173840 A1 | 9/2011 |
| SG | 175229 A1 | 11/2011 |
| SG | 176833 A1 | 1/2012 |
| SG | 178836 A1 | 4/2012 |
| SG | 193484 A1 | 10/2013 |
| TW | 200509870 A | 3/2005 |
| TW | 1231755 B | 5/2005 |
| TW | 200800123 A | 1/2008 |
| TW | 1330075 B | 9/2010 |
| WO | 93/25157 A1 | 12/1993 |
| WO | 2004049981 A3 | 6/2004 |
| WO | 2004051301 A3 | 6/2004 |
| WO | 2005051239 A1 | 6/2005 |
| WO | 2005051240 A1 | 6/2005 |
| WO | 2006058057 A2 | 6/2006 |
| WO | 2006060795 A1 | 6/2006 |
| WO | 2006058057 A8 | 7/2006 |
| WO | 2007041375 A2 | 4/2007 |
| WO | 2007062103 A1 | 5/2007 |
| WO | 2007092841 A2 | 8/2007 |
| WO | 2007109641 A2 | 9/2007 |
| WO | 2007092841 A3 | 11/2007 |
| WO | 2007109641 A3 | 12/2007 |
| WO | 2008101090 A2 | 8/2008 |
| WO | 2008109751 A1 | 9/2008 |
| WO | 2008112996 A1 | 9/2008 |
| WO | 2008101090 A3 | 11/2008 |
| WO | 2008157412 A2 | 12/2008 |
| WO | 2007041375 A3 | 4/2009 |
| WO | 2008157412 A3 | 4/2009 |
| WO | 2009111626 A2 | 9/2009 |
| WO | 2009111639 A1 | 9/2009 |
| WO | 2009111656 A1 | 9/2009 |
| WO | 2009140294 A1 | 11/2009 |
| WO | 2009111626 A3 | 1/2010 |
| WO | 2010099231 A2 | 9/2010 |
| WO | 2010099353 A1 | 9/2010 |
| WO | 2010121147 A1 | 10/2010 |
| WO | 2010099231 A3 | 11/2010 |
| WO | 2011028624 A1 | 3/2011 |
| WO | 2011056995 A2 | 5/2011 |
| WO | 2011072235 A1 | 6/2011 |
| WO | 2011075697 A2 | 6/2011 |
| WO | 2011056995 A3 | 9/2011 |
| WO | 2011075697 A3 | 10/2011 |
| WO | 2011072235 A3 | 12/2011 |
| WO | 2012112694 A1 | 8/2012 |
| WO | 2012112694 A2 | 8/2012 |
| WO | 2012112698 A2 | 8/2012 |
| WO | 2012112701 A2 | 8/2012 |
| WO | 2012112702 A2 | 8/2012 |
| WO | 2012112694 A3 | 1/2013 |
| WO | 2012112701 A3 | 1/2013 |
| WO | 2012112702 A3 | 1/2013 |
| WO | 2013020026 A1 | 2/2013 |
| WO | 2013025814 A1 | 2/2013 |
| WO | 2012112698 A3 | 3/2013 |
| WO | 2013056036 A1 | 4/2013 |
| WO | 2013119790 A1 | 8/2013 |
| WO | 2013119865 A1 | 8/2013 |
| WO | 2013131066 A1 | 9/2013 |
| WO | 2013152341 A1 | 10/2013 |
| WO | 2013155500 A1 | 10/2013 |
| WO | 2013155501 A1 | 10/2013 |
| WO | 2014008444 A1 | 1/2014 |
| WO | 2014035991 A1 | 3/2014 |
| WO | 2014047514 A1 | 3/2014 |

(56) References Cited

OTHER PUBLICATIONS

Gan et al. ("Novel patient-specific navigational template for total knee arthroplasty", Informa UK Ltd, 2011, pp. 288-297) (Year: 2011).*

Murphy et al., "The Planning of Orthopaedic Reconstructive Surgery Using Computer-Aided Simulation and Design", Camp. Med. /mag. and Graphics, 12:33-45, (1988).

U.S. Iannotti et al., U.S. Appl. No. 61/408,324, filed Oct. 29, 2010, entitled "System and Method for Assisting with Attachment of a Stock Implant to a Patient Tissue".

U.S. Iannotti et al., U.S. Appl. No. 61/408,359, filed Oct. 29, 2010, entitled "System and Method for Association of a Guiding Aid with a Patient".

U.S. Iannotti et al., U.S. Appl. No. 61/408,376, filed Oct. 29, 2010, entitled "System and Method for Assisting with Arrangement of a Stock Instrument with Respect to a Patient Tissue".

International Search Report and Written Opinion for PCT/US2011/057957, dated Apr. 18, 2012, pp. 1-11.

Krekel, et al., Interactive Simulation and Comparative Visualisation of the . . . , Data Visualisation Group, Delft Univ. of Technology, pp. 1-13.

Krekel, et al., Combined Surface and Volume Processing for Fused Joint Segmentation, Springer Int'l. Journal of Computer Assisted Radiology and Surgery, pp. 1-24.

Krekel, et al., Visual Analysis of Multi-Joint Kinematic Data, Eurographics/IEEE-VGTC Symposium on Visulatization 2010, vol. 29 (2010), No. 3, pp. 1-10.

Krekel, et al., Evaluation of Bone Impingement Prediction in Preoperative Planning for Shoulder Arthroplasty, Proc. I MechE vol. 223, Part H: J.Engin. in Med., 2009, pp. 1-10.

Botha, et al., Pre-Operative Planning and Intra-Operative Guidance for Shoulder Replacement Surgery, Dagstuhl Publ., pp. 179-195. Ylftekhar.

Taylor et al, "Computer-Integrated Surgery, Technology and Clinical Applications", The MIT Press, Cambridge, MA, London, UK, pp. 451-463.

Hofmann et al, "Natural-Knee II System", Intermedics Orthopedics, Austin, TX, 1995.

* cited by examiner

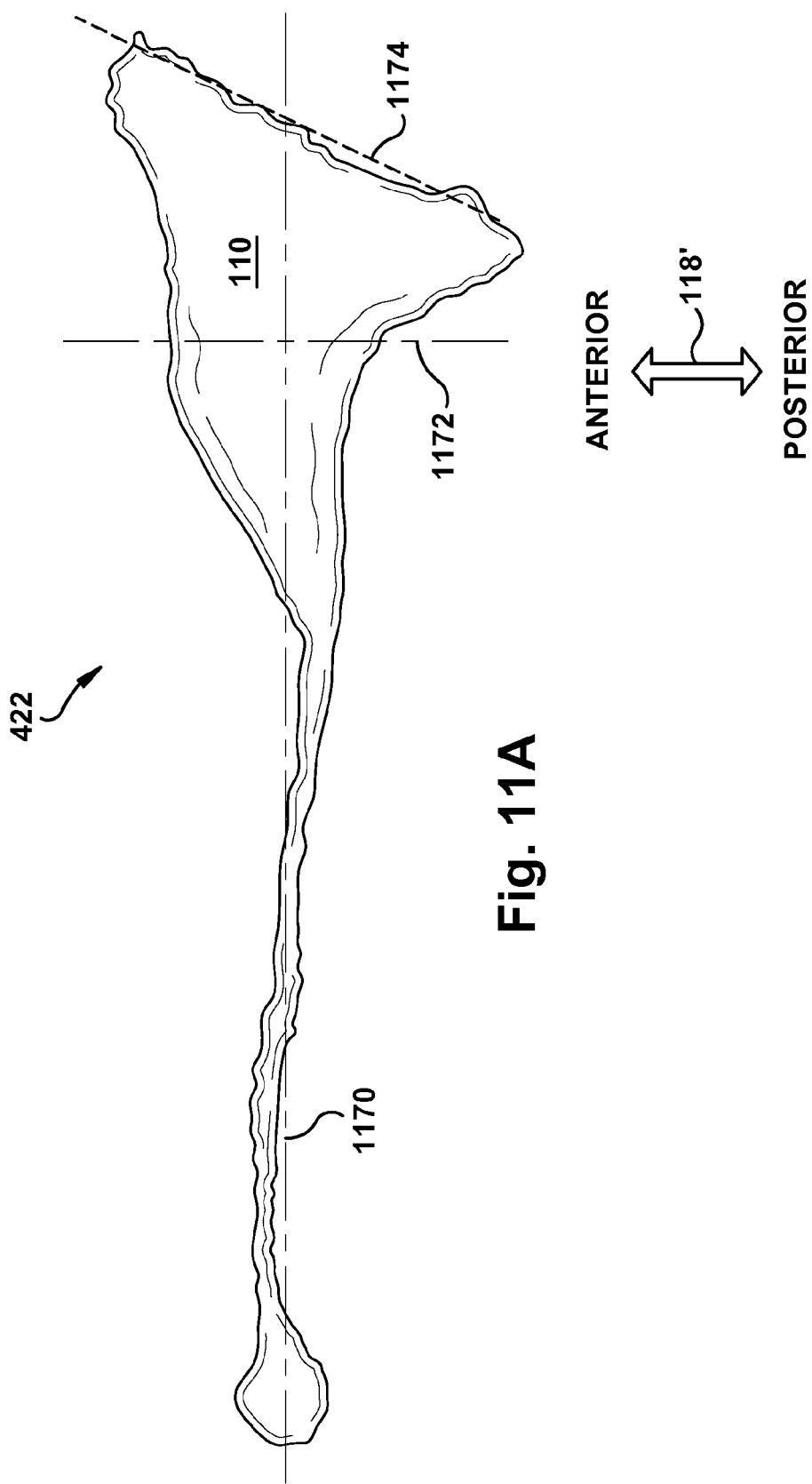

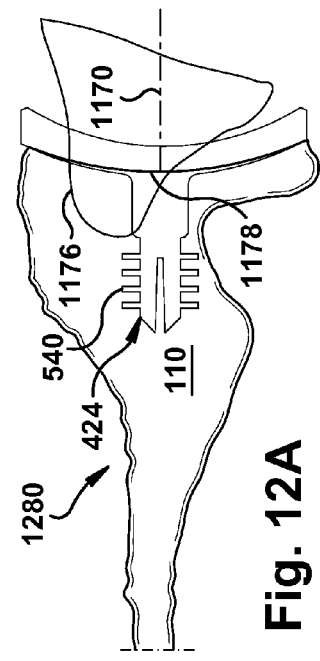
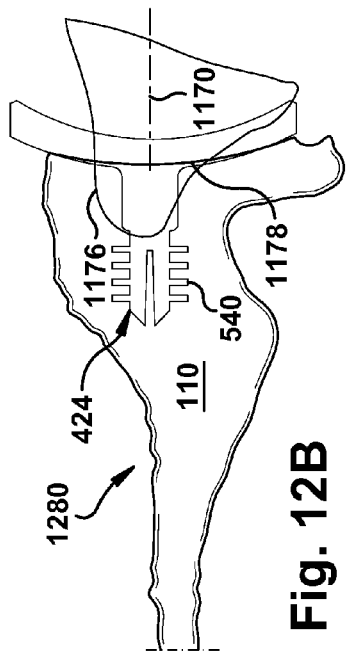
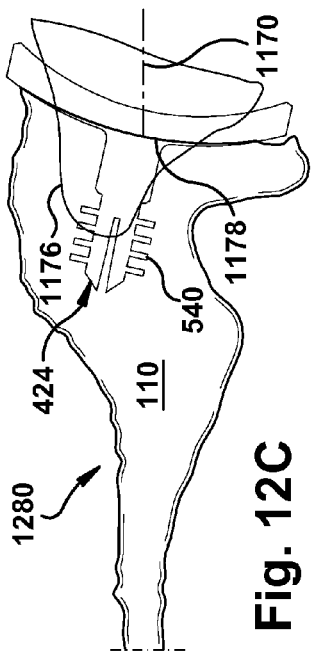
Fig. 12A
Fig. 12B
Fig. 12C
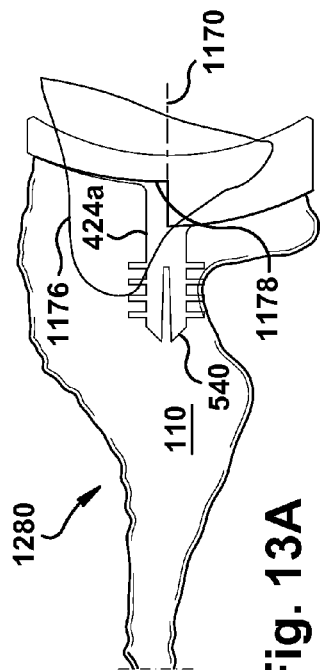
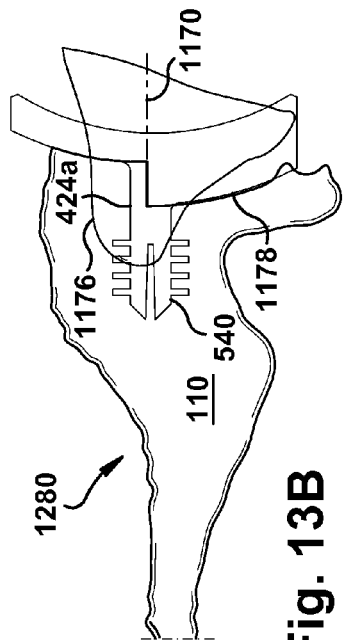
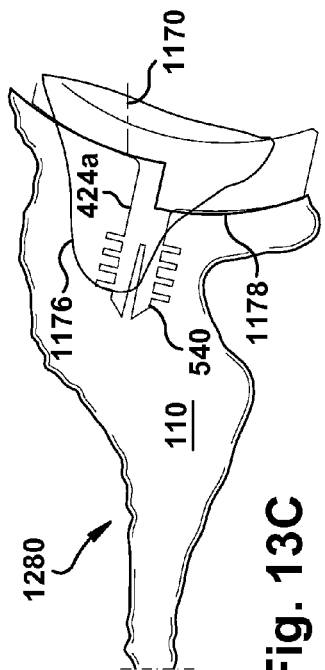
Fig. 13A
Fig. 13B
Fig. 13C

SYSTEM OF PREOPERATIVE PLANNING AND PROVISION OF PATIENT-SPECIFIC SURGICAL AIDS

RELATED APPLICATION

The present application is a continuation of U.S. Non-Provisional application Ser. No. 13/282,550 filed on Oct. 27, 2011 which claims priority on U.S. Provisional Application Ser. No. 61/408,392, filed on Oct. 29, 2010, and incorporated herewith by reference.

TECHNICAL FIELD

The present invention relates to a preoperative planning system and, more particularly, to a system of preoperative planning and provision of patient-specific surgical aids.

BACKGROUND OF THE INVENTION

The scapula, commonly known as the "shoulder blade", is a flat, triangular bone that lies over the back of the upper ribs. A right scapula 100 is depicted in posterior, anterior, and right side views in FIGS. 1A, 1B, and 1C, respectively. The posterior surface of the scapula 100 can be readily felt through a patient's skin. The scapula 100 serves as an attachment point for some of the muscles and tendons of the arm, neck, chest, and back, and aids in the movements of the arm and shoulder. The scapula 100 is also well padded with muscle, so that it may be difficult to palpate boney landmarks. The rear surface of each scapula 100 is divided into unequal portions by a spine 102. This spine 102 leads to a head 104, which ends in the acromion process 106. A coracoid process 108 forms a prominence of the shoulder that curves forward and down below the clavicle (collarbone, not shown). The acromion process 106 joins the clavicle and provides attachments for muscles of the arm and chest muscles. The acromion process 106 is a bony prominence at the top of the scapula 100. On the head 104 of the scapula 100, between the acromion and coracoid processes 106 and 108, is a depression or cavity called the glenoid vault 110, shown partially in dashed line in the Figures. The glenoid vault 110 joins with the head of the upper arm bone (humerus, not shown) in a ball-and-socket manner to enable articulation of the shoulder joint thereby formed. Similarly, though not shown, an acetabulum of the hip joint mates with a head of an upper leg bone (femur) to form an analogous ball-and-socket manner for hip joint articulation.

For treatment of various problems with the shoulder, hip, or other body joint or bone (such as degenerative arthritis and/or traumatic injury), one method of providing relief to a patient is to replace the articulating surfaces with an artificial or prosthetic joint. In the case of a shoulder, the humerus and glenoid vault 110 articulating surfaces are replaced. In the case of a hip, the femur and acetabulum articulating surfaces can be replaced. Both of these examples are of ball-and-socket type joints. Hinge-type joints, such as the knee or elbow, and static/fixed skeletal components, such as the long bones of the arm or leg, as well as interfaces such as those between spinal vertebrae and intervertebral discs, could also be subject to replacement and/or repair by the implantation of artificial or prosthetic components or other fixation devices related to the treatment of fractures, the sequelae of trauma, congenital pathology, or other issues causing a lack of ideal function. For clarity of description, the subject application will be hereafter described as the rehabilitation and/or replacement of a patient's shoulder joint.

In such surgical procedures, pain relief, increased motion, and/or anatomic reconstruction of the joint are goals of the orthopedic surgeon. With multiple variations in human anatomy, prosthetic systems must be carefully designed, chosen, and implanted to accurately replicate the joints that they replace or the bone structures that they aim to change (in any manner).

A shoulder replacement procedure may involve a partial shoulder replacement (not shown) or the total shoulder replacement shown in FIG. 2. In a total shoulder replacement procedure, a humeral component 212 having a head portion is utilized to replace the natural head portion of the upper arm bone, or humerus 214. The humeral component 212 typically has an elongated stem which is utilized to secure the humeral component to the patient's humerus 214, as depicted. In such a total shoulder replacement procedure, the natural bearing surface of the glenoid vault 110 is resurfaced, lined, or otherwise supplemented with a cup-shaped glenoid component 216 that provides a bearing surface for the head portion of the humeral component 212. The depicted total shoulder replacement of FIG. 2 is an "anatomical" shoulder replacement. A "reverse" shoulder replacement is also known in the art.

Standard prosthetic glenoid components 216 are available in a number of different sizes and configurations. However, most are designed for use in an scapula having minimal bone loss or deformity. When the scapula has bone loss and/or significant pathology due to disease or trauma, the standard glenoid component 216 may be difficult to implant and/or may not enable desired shoulder function, if it cannot be implanted in a preferred manner. The surgeon may thus need to substantially modify the patient's glenoid vault 110 during surgery in an attempt to make the standard glenoid component 216 fit into the glenoid vault. Pre-surgical planning tools are available to help the surgeon anticipate the changes which will be needed to reform the patient's pathological anatomy. However, the surgeon cannot always readily determine whether even a remodeled glenoid vault 110 will fit as desired with a standard prosthesis because the surgeon does not know how a "normal" glenoid vault 110 (for which the standard prosthesis is designed) should be shaped for that patient.

It is known to use computer aided design ("CAD") software to design custom prostheses based upon imported data obtained from a computerized tomography ("CT") scan of a patient's body. For example, mirror-imaged CT data of a patient's contralateral "normal" joint could be used, if the contralateral joint does not also display a pathological anatomy. However, using a unique prosthesis design for each patient can result in future biomechanical problems resulting from a non-proven design and takes away the familiarity that the surgeon will likely have with standardized prosthesis designs. Thus, prosthesis designs that are entirely customized are considered sub-optimal solutions.

Further, detailed preoperative planning, using two- or three-dimensional images of the shoulder joint, often assists the surgeon in compensating for the patient's anatomical limitations. During the surgery, for example, an elongated pin may be inserted into the surface of the patient's bone, at a predetermined trajectory and location, to act as a passive landmark or active guiding structure in carrying out the preoperatively planned implantation. This "guide pin" may remain as a portion of the implanted prosthetic joint or may be removed before the surgery is concluded. This type of pin-guided installation is common in any joint replacement procedure—indeed, in any type of surgical procedure in which a surgeon-placed fixed landmark is desirable.

In addition, and again in any type of surgical procedure, modern minimally invasive surgical techniques may dictate that only a small portion of the bone or other tissue surface being operated upon is visible to the surgeon. Depending upon the patient's particular anatomy, the surgeon may not be able to precisely determine the location of the exposed area relative to the remaining, obscured portions of the bone through mere visual observation. For example, in a shoulder surgery, the scapula 100 is mobile along the chest wall and it therefore may be difficult to define the fixed relationship of the glenoid vault 110 to the body of the scapula 100 (i.e., using the plane of the scapula as a reference to the glenoid vault) and/or the body of the scapula to an external coordinate system in the operating room. These factors, particularly in a minimally invasive surgical procedure, may make it difficult for the surgeon to orient the glenoid vault during surgery. Again, a guide pin may be temporarily or permanently placed into the exposed bone surface to help orient the surgeon and thereby enhance the accuracy and efficiency of the surgical procedure.

One goal of shoulder surgery may be to modify the pathologic bone to correct pathologic version to be within the normal range or the normal version of the patient's native anatomy before the bone loss occurred. During surgery, and particularly minimally invasive procedures, the plane of the scapula may be difficult or impossible to determine by direct visual inspection, resulting in the need for assistive devices or methods to define both the pathologic version present at the time of surgery and the intended correction angle.

It is generally believed that there is a preferred orientation for the glenoid component 216 to provide a full range of motion and to minimize the risk of dislocation. Some example orientations of the glenoid component 216 relative to the glenoid face are about 5.degree. of anteversion to about 15.degree. of retroversion; average version is about 1-2.degree. of retroversion. This broadly replicates the natural angle of the glenoid. However, the specific angular orientation of the glenoid portion varies from patient to patient.

With a view to overcoming these and other disadvantages, some arrangements have been recently suggested in which a three-dimensional intraoperative surgical navigation system is used to render a model of the patient's bone structure. This model is displayed on a computer screen and the user is provided with intraoperative three-dimensional information as to the desired positioning of the instruments and the glenoid component 216 of the prosthetic implant. However, surgical navigation arrangements of this type are not wholly satisfactory since they generally use only a low number of measured landmark points to register the patient's anatomy and to specify the angle of the prosthetic implant component (e.g., a glenoid component 216), which may not provide the desired level of accuracy. Further, the information provided by such systems may be difficult to interpret and may even provide the user with a false sense of security. Moreover, these systems are generally expensive to install and operate and also have high user training costs.

Various proposals for trial prosthetic joint components have been made in an attempt to overcome the problems associated with accurately locating the glenoid component 216 of the prosthetic implant. While these trial systems may help with checking whether the selected position is correct, they are not well-suited to specify the correct position initially, and thus there still is user desire for a system which may assist a user in placement of prosthetic implant component in a prepared native tissue site.

Finally, due to factors such as the high cost of operating room time and the patient detriment sometimes posed by lengthy surgeries, the surgeon or other user may wish to simulate a surgical procedure during preoperative planning, in order to become familiar with the tasks that will be required and possibly reduce the time and/or actions needed to perform the surgery.

In summary, preoperative planning and/or simulation, regardless of the planning tasks undertaken or the nature of the changes to be made to the patient's native tissue, will generally reduce the need for intraoperative imaging in most surgical procedures and should result in decreased operative time and increased positional accuracy, all of which are desirable in striving toward a positive patient outcome.

SUMMARY OF THE INVENTION

In an embodiment of the present invention, a method of preoperative planning, the method comprises: creating a virtual model of a native patient tissue; placing a virtual device into a desired device orientation relative to the virtual model of the native patient tissue; specifying at least one structural change to the native patient tissue to facilitate placement of the virtual device in the desired device orientation; creating a virtual model of an altered patient tissue responsive to the specifying at least one structural change to the native patient tissue; and fabricating a tangible representation of a bone using the virtual model of the altered patient tissue.

In an embodiment of the present invention, a method of preoperative planning and provision of patient-specific surgical aids is described. A device for placement in engagement with a native patient tissue is chosen. A predetermined device orientation for the device with respect to the native patient tissue is virtually specified. At least one landmark is virtually placed in a predetermined landmark orientation with respect to the predetermined device orientation. A patient-specific placement guide is virtually modeled, the patient-specific placement guide being simultaneously mated with the device and registered with at least one landmark when the device is in the predetermined device orientation. A patient-specific template is virtually modeled, the patient-specific template being configured to mate with the native patient tissue, the patient-specific template having a landmark guiding feature configured to place the landmark in the predetermined landmark orientation when the patient-specific template is mated with the native patient tissue. A physical version of the patient-specific placement guide is created. A physical version of the patient-specific template is created.

In an embodiment of the present invention, a computer readable medium is described. The computer readable medium has computer executable instructions for receiving scanned image data based on an imaging scan of a native patient tissue. An image of the native patient tissue based on the received scanned image data is displayed. Placement of an image of a selected device is displayed over the image of the native patient tissue. The image of the selected device over the image of the native patient tissue is reoriented into a predetermined device orientation. Placement of an image of at least one selected landmark is displayed in a predetermined landmark orientation over the image of the native patient tissue. Placement of an image of a selected guide blank is displayed in a predetermined guide orientation over the image of the native patient tissue and the image of the selected device, when the image of the selected device is in the predetermined device orientation. The selected guide blank is provided with at least one orienting feature, the provided orienting feature being registered with at least one selected landmark when the image of a selected guide blank is in the predetermined guide orientation and the image of the selected device is in the predetermined device orientation. A physical guide is fabricated from the selected guide blank having the provided orienting feature.

In an embodiment of the present invention, a method of preoperative planning and provision of at least one patient-specific surgical aid is described. A virtual model of a native patient tissue is created. A physical model of the native patient tissue as a tangible representation of the virtual model of the native patient tissue is created. The physical model of the native patient tissue includes at least one information feature providing clinically useful information to the user.

BRIEF DESCRIPTION OF THE DRAWINGS

For a better understanding of the invention, reference may be made to the accompanying drawings, in which:

FIGS. 11A-11B are schematic views depicting a use environment for the embodiment of FIG. 3;

FIGS. 12A-12C are schematic views depicting placement options for one element of the embodiment of FIG. 3 in a first configuration;

FIGS. 13A-13C are schematic views depicting placement options for one element of the embodiment of FIG. 3 in a second configuration;

DESCRIPTION OF EMBODIMENTS

The patient tissue is shown and described herein at least as a scapula 100 and the prosthetic implant component is shown and described herein at least as a glenoid component 216, but the patient tissue and corresponding prosthetic implant component could be any desired types such as, but not limited to, hip joints, shoulder joints, knee joints, ankle joints, phalangeal joints, metatarsal joints, spinal structures, long bones (e.g., fracture sites), or any other suitable patient tissue use environment for the present invention. For example, the prosthetic implant component could be an internal fixation device (e.g., a bone plate), a structure of a replacement/prosthetic joint, or any other suitable artificial device to replace or augment a missing or impaired part of the body.

Figure 10:
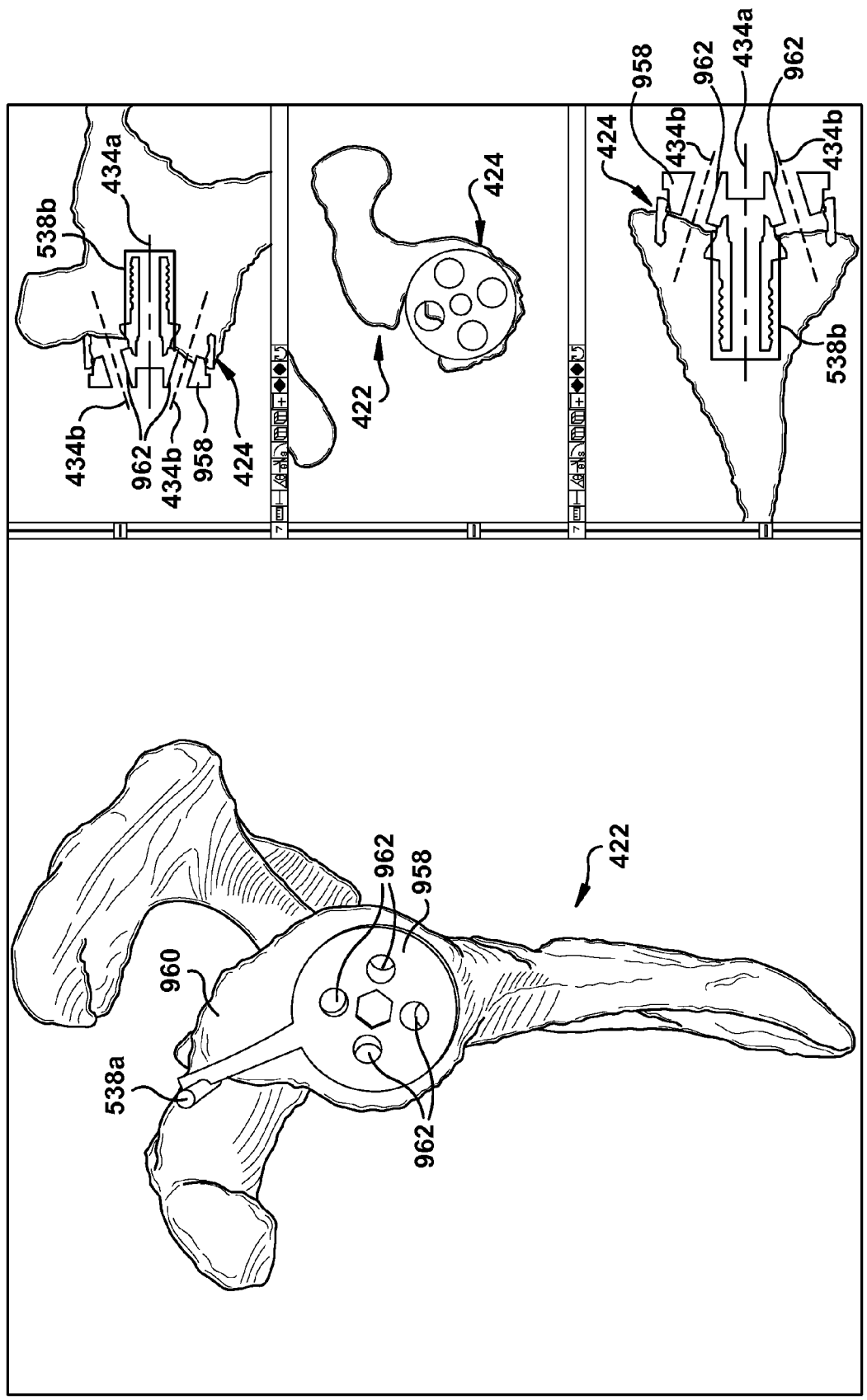

The term "lateral" is used herein to refer to a direction indicated by directional arrow 118 in FIG. 10; the lateral direction in FIG. 10 lies substantially within the plane of the drawing and includes all of the superior, inferior, anterior, and posterior directions. The term "longitudinal" is used herein to refer to a direction defined perpendicular to the plane created by directional arrow 118, with the longitudinal direction being substantially into and out of the plane of the drawing in FIG. 10 and representing the proximal (toward the medial line of the body) and distal (out from the body) directions, respectively.

Figure 1A:
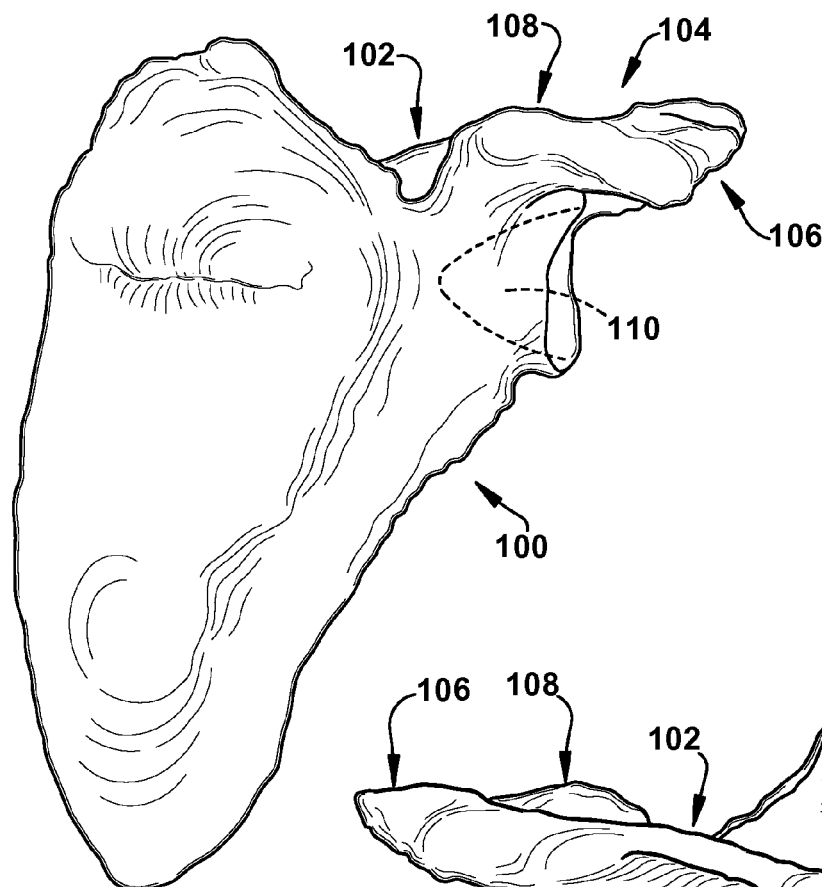
FIG. 1A is an anterior view of a right scapula.
Figure 1B:
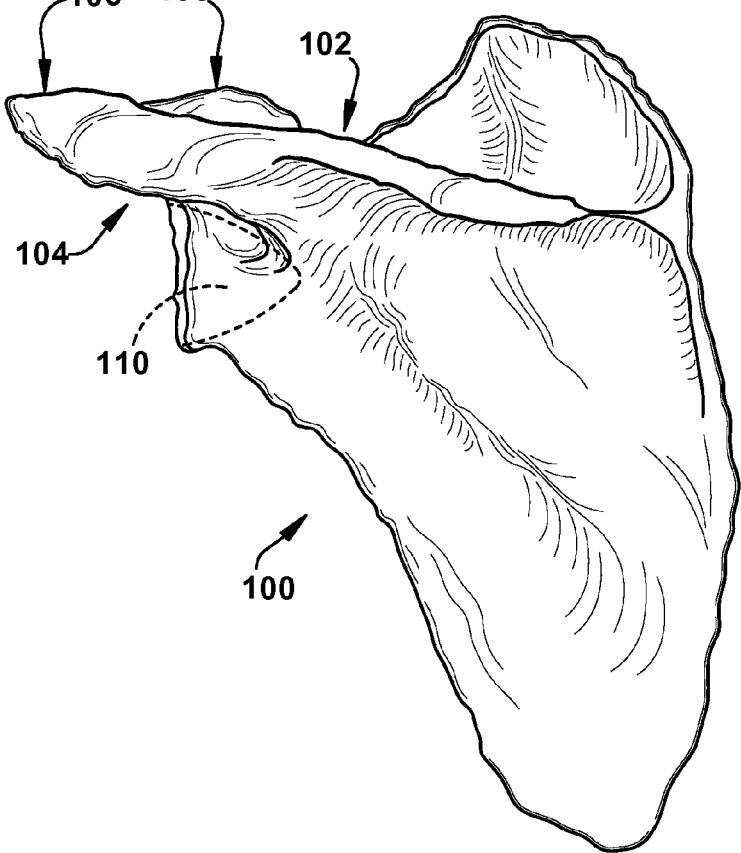
FIG. 1B is a posterior view of the scapula of FIG. 1A.
Figure 1C:
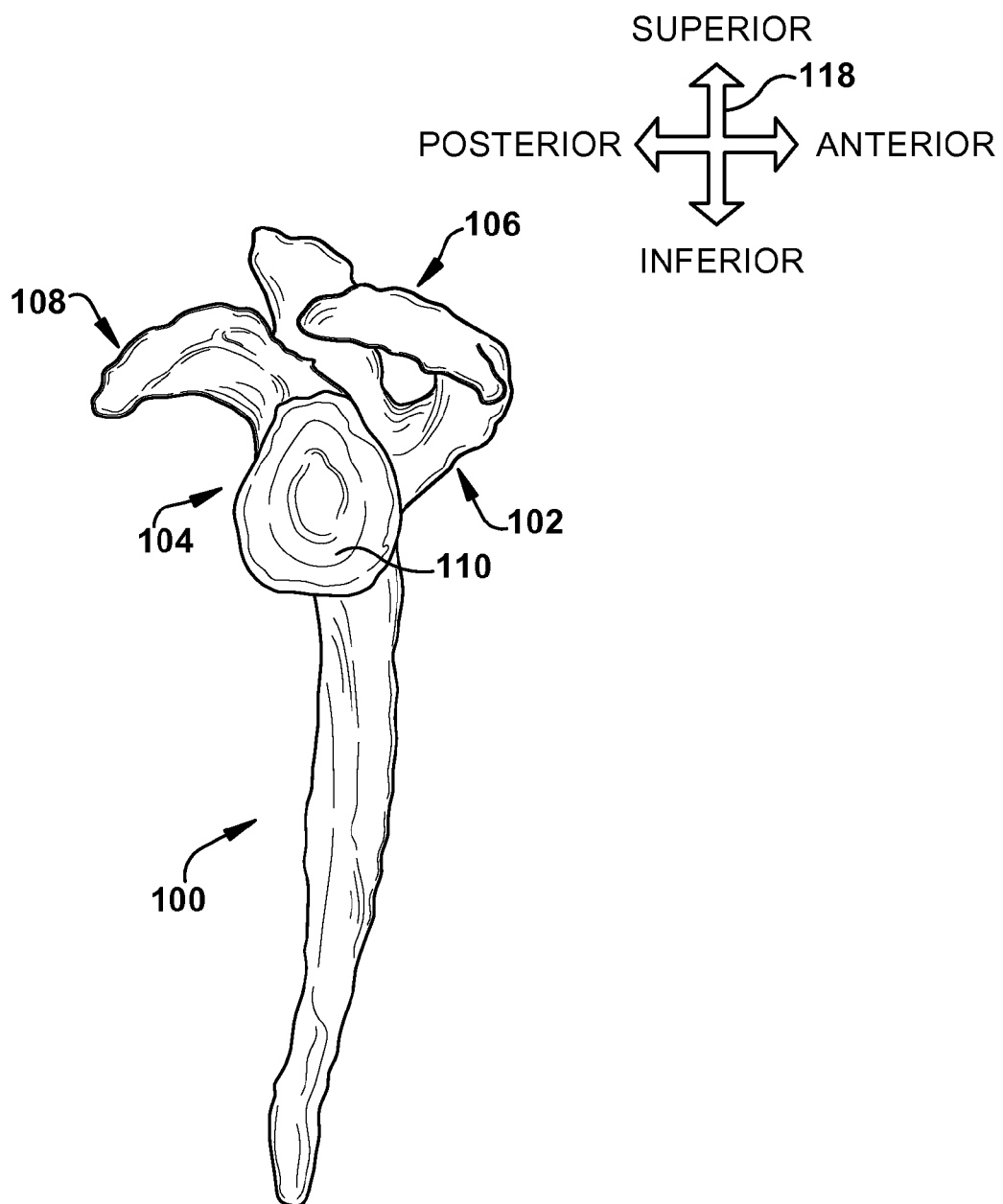
FIG. 1C is a side view of the scapula of FIG. 1A.
Figure 2:
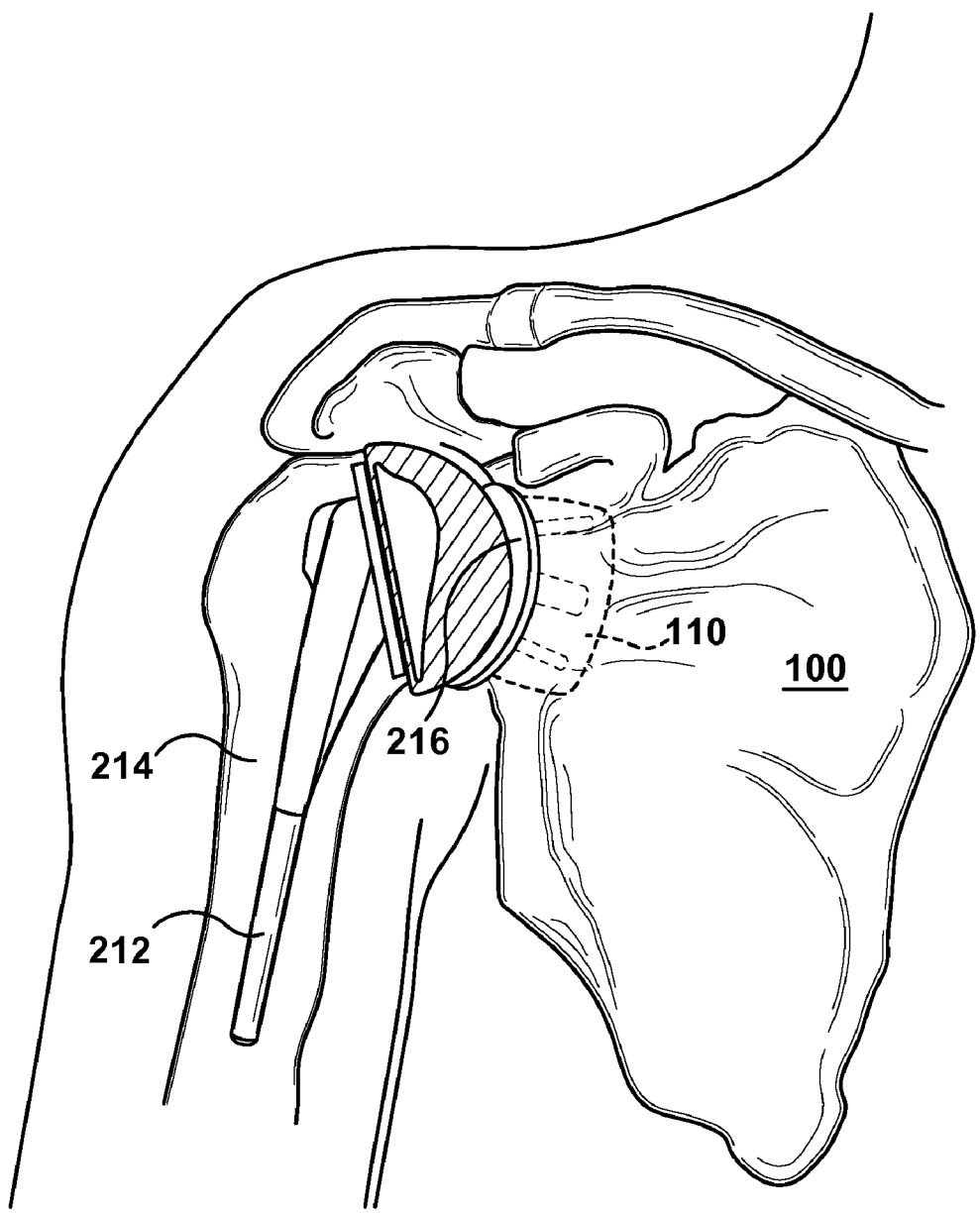
FIG. 2 is a partial sectional anterior view of a prosthetic shoulder joint in a patient.
Figure 3:
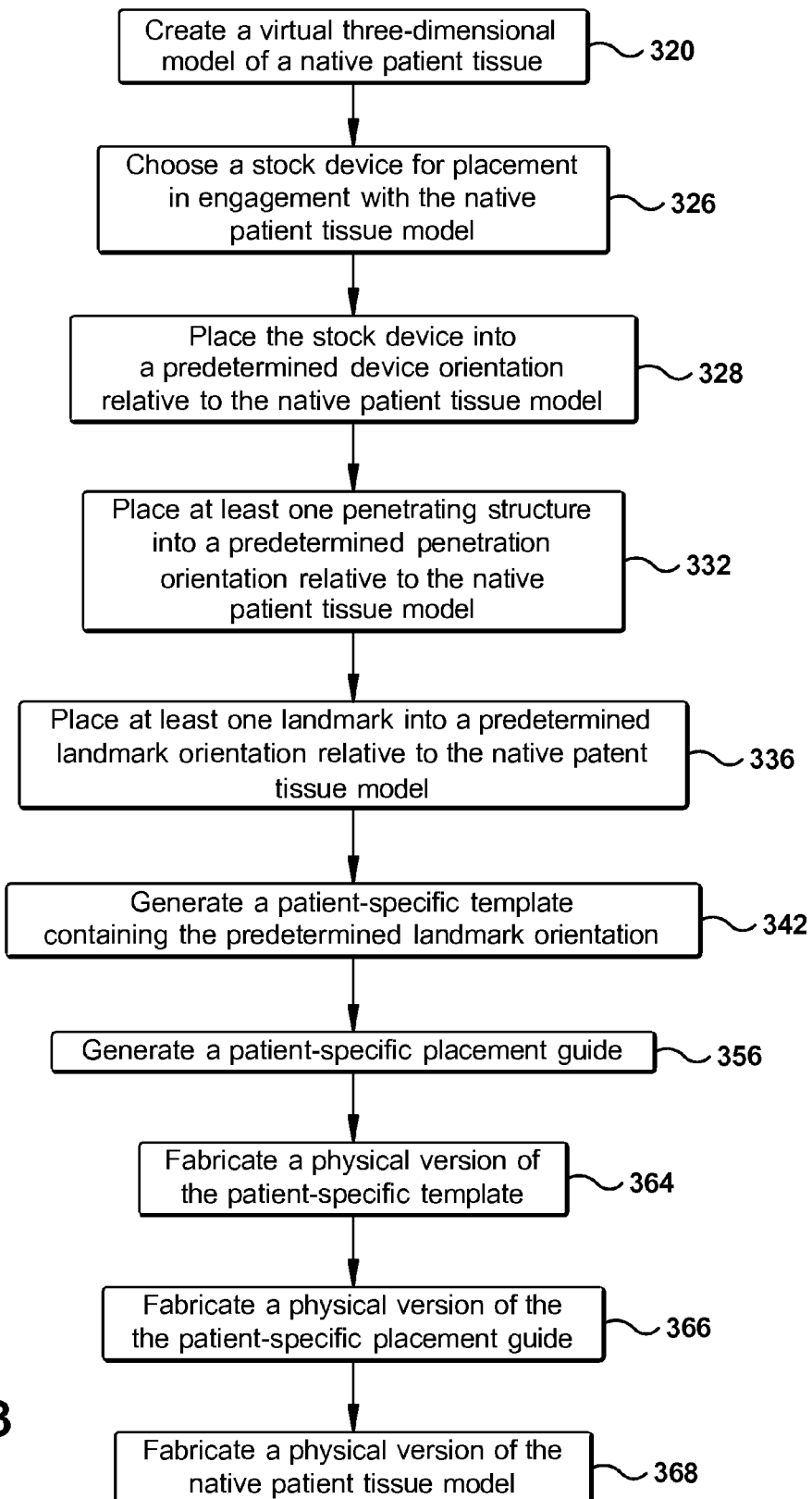
FIG. 3 is a flowchart describing one embodiment of the present invention.

In accordance with the present invention, FIG. 3 is a flowchart depicting one example series of steps of a method of preoperative planning and provision of patient-specific surgical aids. In first action block 320, a virtual three-dimensional model of a native patient tissue is created. A "native" patient tissue herein is used to reference the status of the actual, physical patient tissue at the time that the surgery is being planned. For example, the native patient tissue may have been in the "native" state from birth, or may instead be subject to a congenital or acquired deficiency and accordingly be in an altered state as compared to the patient tissue originally present in the patient. Regardless of the mechanism by which the patient tissue came into the "native" condition, the "native" patient tissue is used herein to reference the expected state of the patient tissue at the time of the operation—when the user cuts into the patient's body, the native patient tissue is what will be found at the surgical site.

The virtual model of the native patient tissue may be based upon, for example, scanned image data taken from an imaging scan of the native patient tissue. The term "model" is used herein to indicate a replica or copy of a physical item, at any relative scale and represented in any medium, physical or virtual. The patient tissue model may be a total or partial model of a subject patient tissue, and may be created in any suitable manner. For example, and as presumed in the below description, the patient tissue model may be based upon computer tomography ("CT") data imported into a computer aided drafting ("CAD") system. Additionally or alternatively, the native patient tissue model may be based upon digital or analog radiography, magnetic resonance imaging, or any other suitable imaging means. The patient tissue model will generally be displayed for the user to review and manipulate preoperatively, such as through the use of a computer or other graphical workstation interface. While this description presumes a three-dimensional model, one of ordinary skill in the art could use a two-dimensional model in a similar manner to that shown and described herein, without harm to the present invention. An example of a virtual model of the native patient tissue is the native patient tissue model 422 shown in FIGS. 4-10.

FIGS. 4-10 pictorially depict the preoperative planning procedure described in the FIG. 3 flowchart. FIGS. 4-10 are example user views of a computer program and/or system for implementing a method of using the present invention, with a perspective view on the left side of each Figure and coronal, sagittal (looking distally from underneath the perspective view, as shown), and transverse views, respectively, from top to bottom on the right side of each Figure.

During preoperative planning with a system such as that described, the user can view the native patient tissue model 422 and, based upon knowledge of other patient characteristics (such as, but not limited to, height, weight, age, and activity level), choose a desired device, described hereafter as a stock device 424, for use in the surgical procedure. This use may include placement in engagement with a native patient tissue model 422, as shown in second action block 326 of FIG. 3. Visually, such as in the user view of FIG. 4, an image of the selected desired stock device 424 may be placed over the native patient tissue model image.

A desired device could be the depicted stock prosthetic implant, a custom prosthetic implant, a stock or custom instrument (not shown), or any other desired item. Because three-dimensional image models are available of many instruments and prosthetic implants, whether stock or custom, the user may be able to "install" the instrument or prosthetic implant virtually in the native patient tissue model 422 via the preoperative computer simulation described herein. During such a simulation, the user can automatically and/or manually adjust or reorient the position of the virtual stock device 424 with respect to the virtual native patient tissue model 422, even to the extent of simulating the dynamic interaction between the two, as may be helpful to refine the selection, placement, and orientation of the stock device for a desired patient outcome. The stock device 422 may be chosen from a library of available stock devices, with the choice based upon any factor or characteristic desired.

The term "stock" is used herein to indicate that the component indicated is not custom-manufactured or -configured for the patient, but is instead provided as a standard inventory item by a manufacturer. A particular stock component may be selected automatically by the system and/or manually by the user from a product line range (e.g., the aforementioned library) of available components, optionally with the user specifying a desired configuration, general or particular size (e.g., small, medium, large, or a specific measurement), material, or any other characteristic of the component. Indeed, the stock component could be manufactured only after the user has selected the desired options from the range of choices available. However, the stock component is differentiated from a custom-manufactured or bespoke component in that the stock component is agnostic and indifferent regarding a particular patient anatomy during the design and manufacturing processes for an instrument, prosthetic implant, or other component intended for that patient, while the patient anatomy is an input into at least one design and/or manufacturing process for a custom-manufactured component. The following description presumes the use of a stock prosthetic implant and stock instrument, though one of ordinary skill in the art will be able to provide for the use of the present invention with a custom-manufactured prosthetic implant or instrument, instead.

Figure 4:
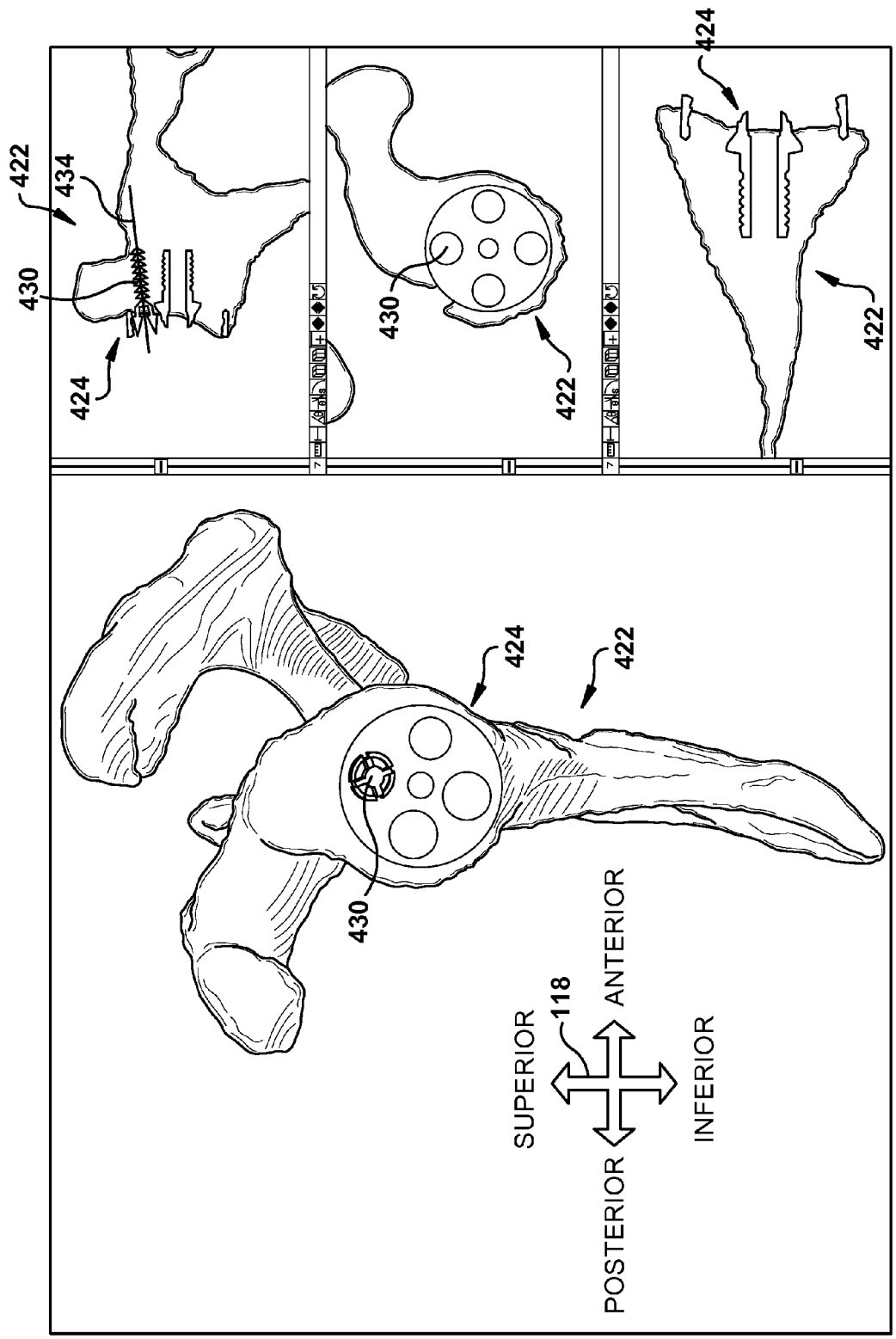
FIGS. 4-10 are example user views of a program for generating the embodiment of FIG. 3.

At third action block 328 of FIG. 3, the stock device 424 is placed, or reoriented, into a predetermined device orientation relative to the native patient tissue model 422, to achieve the position shown in FIG. 4. An orientation of a structure, as used herein, includes both the absolute location of the structure upon or with respect to another structure and the arrangement or positioning in space of the structure (e.g., rotation, pitch, yaw, camber, or any other placement-related variable of the structure).

The system may place the stock device 424 into the predetermined device orientation automatically by the system and/or manually by the user, based upon any suitable criteria. For example, the system may provide at least two optional device orientations and compare the optional device orientations to each other based upon any desired device property(ies), in a weighted or unweighted manner. Device properties that could factor into the comparison include at least one of device size, device shape, device material, number of fasteners to be used, type of fasteners, size of fasteners, shape of fasteners, amount of patient tissue alteration, type of patient tissue alteration, orientation of the stock device relative to an other stock device (e.g., orientation of one part of a prosthetic joint relative to another part of the prosthetic joint which has already been [virtually] placed with respect to the native patient tissue model), and physical quality of the native patient tissue. A plurality of optional device orientations could be compared to one another based on these or any other suitable factors, in any suitable manner (e.g., using a decision algorithm or comparison scheme). It is contemplated that certain device properties may be more important than others, and that the comparisons will be made automatically by the system and/or manually by the user to allow for compromises—if needed—on certain device properties in order to strive for a better overall outcome.

Once the comparison(s) is (are) made, the user and/or system chooses an optional device orientation based upon the comparison and designates the chosen optional device orientation as the predetermined device orientation. The predetermined device orientation of the stock device 424 with respect to the native patient tissue model 422 is shown in the FIG. 4 view. As is especially apparent in the coronal (top right) and transverse (bottom right) portions of FIG. 4, there may be some overlap or superposition between the stock device 424 and the native patient tissue model 422. This superposition is permissible in the virtual environment of the described system and may helps to indicate areas of the native patient tissue model 422 which could be targeted for alteration during placement of the stock device 424.

Once a chosen stock device 424 has been virtually placed in a desired orientation with respect to the native patient tissue model 422 (it will be understood that some mechanical modification might need to be made to the actual native patient tissue to accomplish this implant placement in situ), the placement of any fasteners or other penetrating structures 430 (e.g., a drill, guide pin, or other surgical tool), when present, may also be planned through the use of the computer simulation. Consideration of the location, amount, and pathology of the patient tissue, any of the above device properties, or any other desired factors, may be taken into account in this optional penetrating structure 430 planning. The penetrating structure(s) 430 may be chosen from a library of available penetrating structures.

Manually and/or with automatic computer assistance, the user can experiment with various fastener sizes, placements, and orientations for securing the stock prosthetic implant to the patient tissue, and/or with various other types of penetrating structure 430 insertions into the native patient tissue model 422 similarly to the previously described device placement, until reaching at least one predetermined penetration orientation (such as that shown in FIG. 4) for at least one penetrating structure(s) 430 to be used with the surgical procedure being planned, as described in fourth action block 332 of the FIG. 3 flowchart. When the penetrating structure 430 positioning has been finalized, with the stock device 424 virtually positioned in a predetermined device orientation with respect to the patient tissue, a location and target trajectory 434 may be defined for each of the penetrating structures 430 present (if any) to follow during installation. The term "trajectory" is used herein to indicate an invisible line along which an elongate body will travel to reach the predetermined penetration orientation.

Once the predetermined device orientation and any desired predetermined penetration orientation(s), when present, are known, the displayed images of the selected stock device 424 and/or of any included penetrating structures 430 may be removed from the displayed image of the native patient tissue model 422, for greater clarity in following portion(s) of the preoperative planning system. The displayed images of the selected stock device 424 and/or of any included penetrating structures 430 may be reinstated and re-removed, as desired, during any phase of the below operations.

Figure 5:
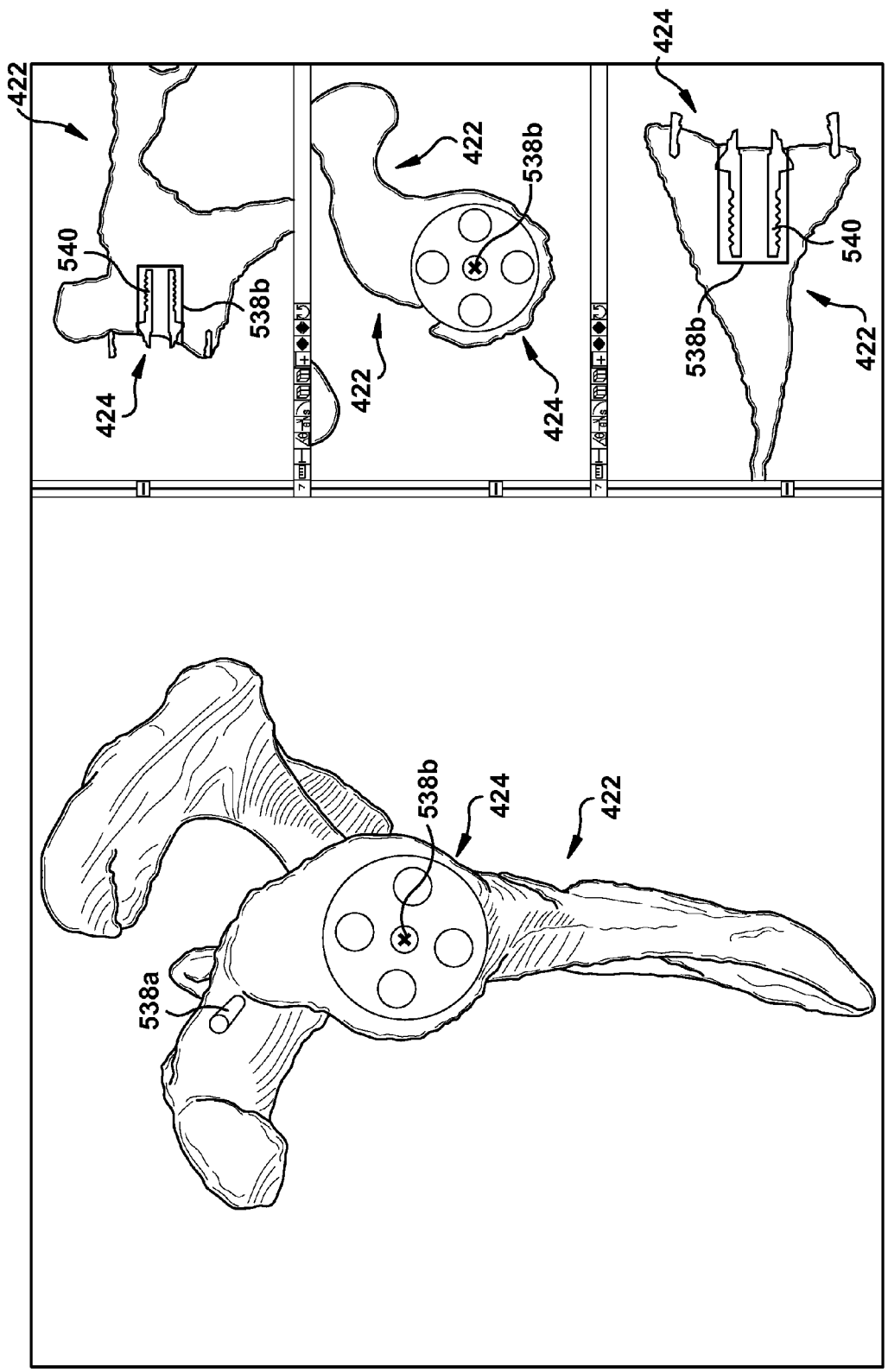

As shown in fifth action block 336 of FIG. 3, at least one landmark 538 (shown in FIG. 5) may be placed in at least one predetermined landmark orientation relative to the native patient tissue model 422. The landmark(s) 538, when present, represent a chosen point in space and/or indicate a chosen direction/orientation relative to the native patient tissue model 422 and are used to convey positional information to the user during a surgical procedure. For example, a guide pin is displayed as a three-dimensional landmark 538a spaced apart from the stock device 424 over the image of the native patient tissue model 422 in FIG. 5, while an aperture or cavity formed in the native patient tissue model is shown as a two-dimensional landmark 538b (i.e., represented by a cross mark when seen from above or below) corresponding to a central portion of the stock device in FIG. 5. In fact, the "negative" aperture-type landmark 538b of FIG. 5 is configured to receive a device shaft 540 of the stock device 424, which helps to locate and stabilize the stock device with respect to the native patient tissue model 422. One of ordinary skill in the art would readily be able to instead provide a "positive" pin- or shaft-type landmark (not shown) protruding from the native patient tissue model 422 and adapted to be received in a cavity (not shown) of another type of device, in an axle-type manner.

Regardless of the number, location, type, or any other characteristics of the provided landmark(s) 538, it is contemplated that the user will want to transfer the landmarked information to the actual patient tissue during the surgical procedure. To that end, a patient-specific template may be created using the system described herein. The landmark 538 could also or instead be placed during the surgical procedure using a robotic surgical aid, adjustable reusable (e.g., "dial-in") tools, intraoperative imaging, or any other suitable placement aid.

Figure 6:
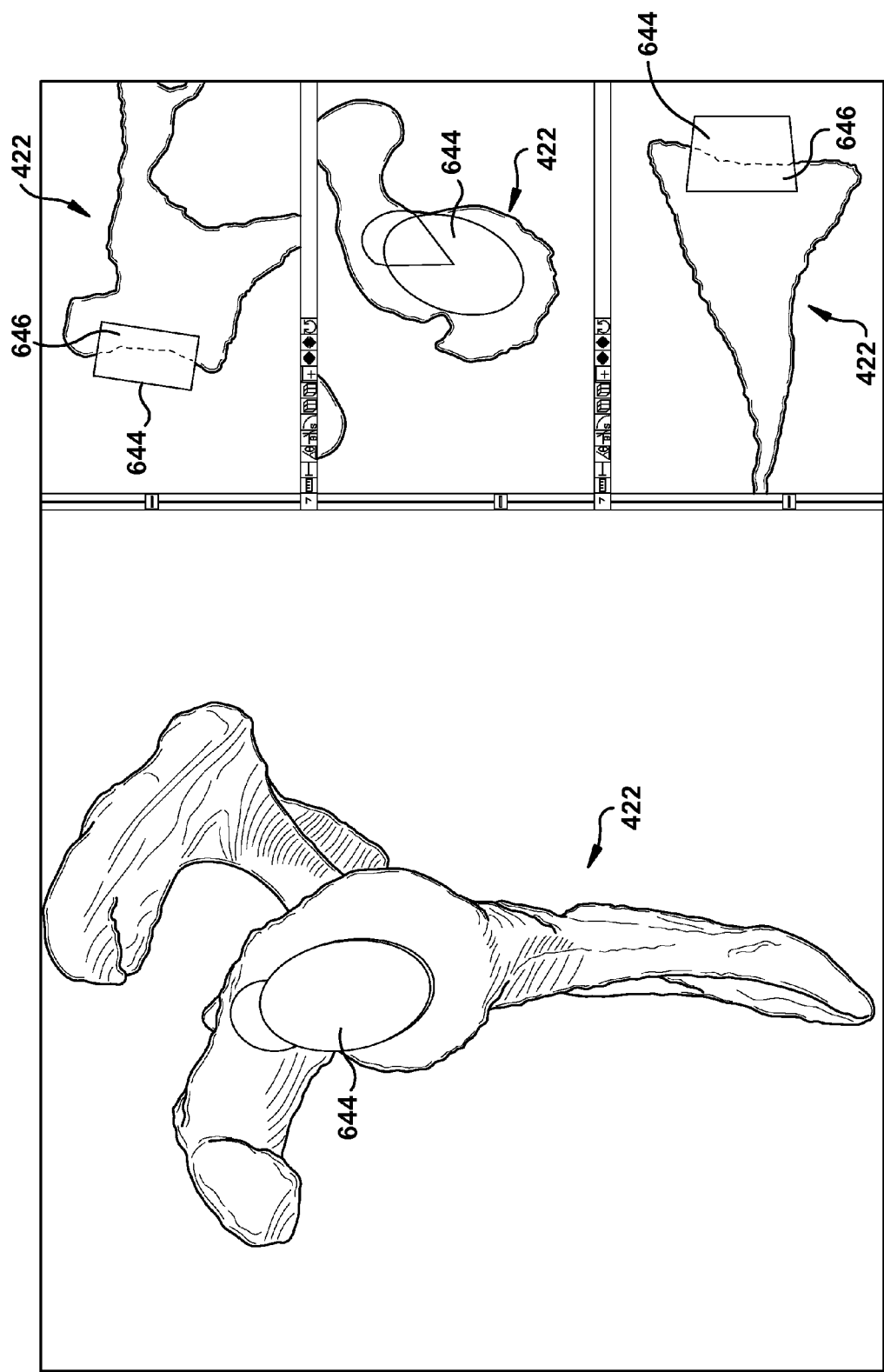
Figure 7:
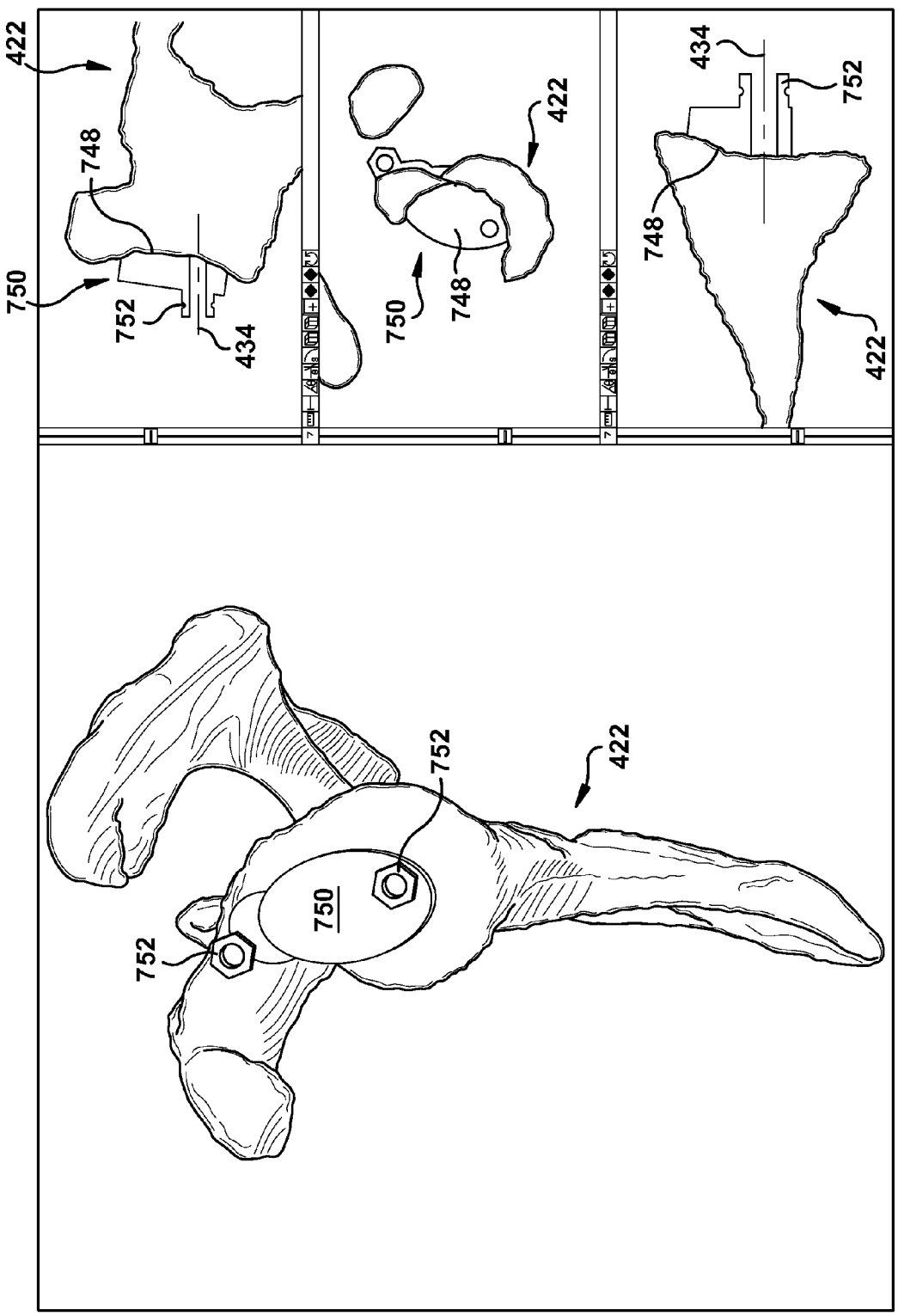
Figure 8:
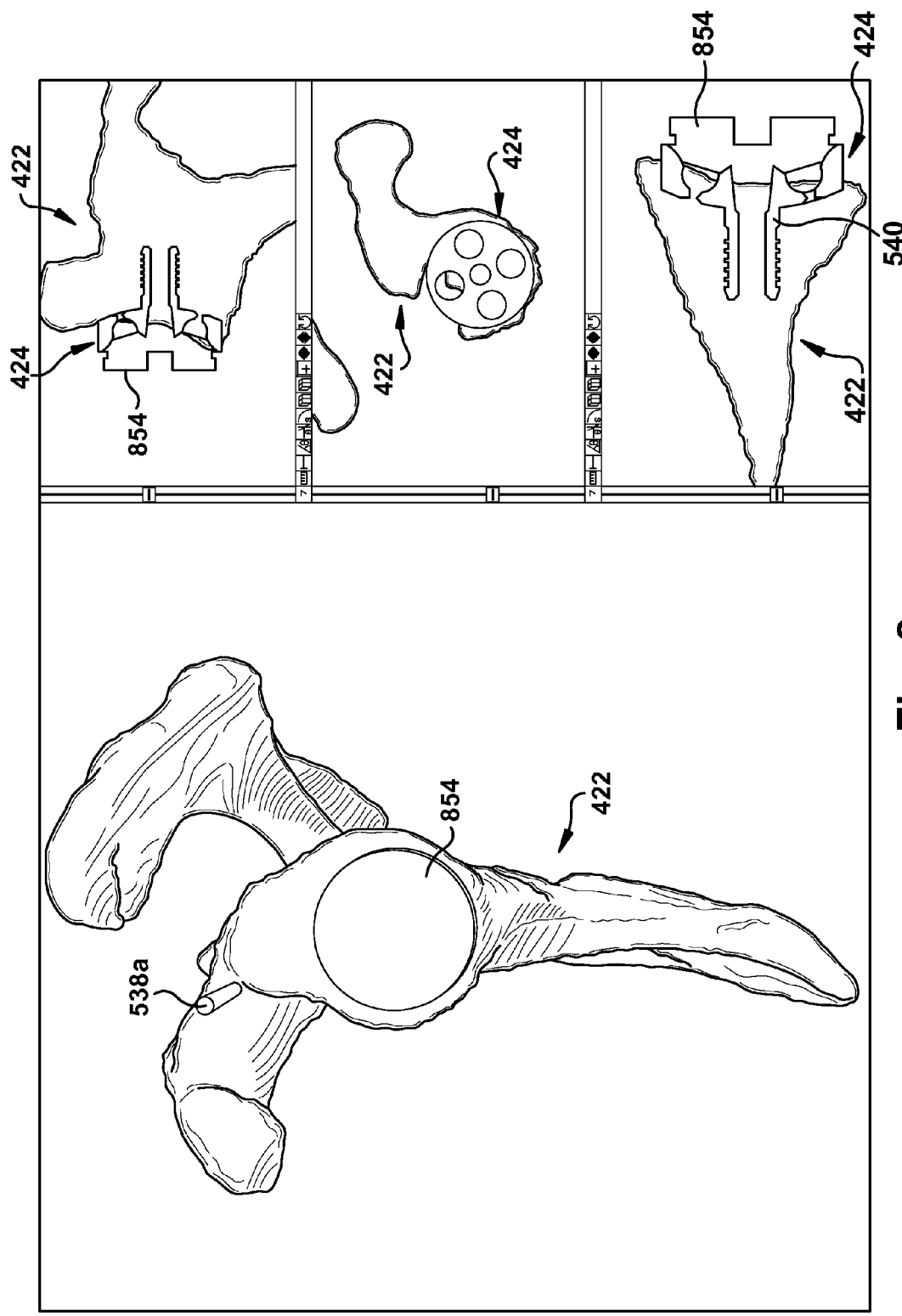

As shown at sixth action block 342 of FIG. 3, a patient-specific template is generated, which may be accomplished by the system with steps represented in user views such as the sequence of FIGS. 6-7. As shown in FIG. 6, a template blank 644 is placed into a desired (final) predetermined template orientation with respect to the native patient tissue model 422. The template blank 644 may be selected, automatically and/or manually, from a library of available template blanks and may be placed, again automatically and/or manually, into the predetermined template orientation based upon any of the above device properties or any other desired factors.

As is particularly apparent in the coronal (top right) and transverse (bottom right) portions of FIG. 6, at least a portion of the native patient tissue model 422 and at least a portion of the template blank 644 (virtually) overlap to create a superposed volume 646 of space which is occupied by both the native patient tissue model and the template blank. Since this superposed volume 646 is impracticable during the actual physical surgical procedure, the superposed volume 646 is (again, virtually) removed from the template blank 644 to create a mating surface 748 of the template blank adjacent the native patient tissue model 422. In other words, the system adjusts the dimensions of the bottom template surface 748 to mate with a surface of the native patient tissue model 422. The term "mate" is used herein to indicate a relationship in which the contours of two structures are at least partially matched or coordinated in at least two dimensions.

The mating surface 748 may be seen in particularly the coronal (top right) and transverse (bottom right) portions of FIG. 7. The patient-specific template 750 may be, for example, the type disclosed in co-pending U.S. patent application No. to be determined, filed Oct. 27, 2011, titled "System and Method for Association of a Guiding Aid with a Patient Tissue" and claiming priority to U.S. Provisional Patent Application No. 61/408,359, filed Oct. 29, 2010 and titled "System and Method for Association of a Guiding Aid with a Patient Tissue", the entire contents of both of which are incorporated herein by reference.

Regardless of its nature, the patient-specific template 750 virtually contains or embodies at least one predetermined landmark orientation and has at least one landmark guiding feature 752 configured to place a landmark 538 in the predetermined landmark orientation when the patient-specific template 750 is mated with the native tissue model 422. As shown in FIG. 7, at least one landmark guiding feature 752 is an aperture through the patient-specific template 750 which is configured to guide a penetrating structure, such as a guide pin or drill bit, into the native patient tissue model 422 at a predetermined penetration location and with a specified target trajectory 434.

When the landmark 538 is a two-dimensional landmark such as a marking on the surface of the native patient tissue, the target trajectory 434 of the landmark guiding feature 752 will likely be of little to no import. In contrast, when the landmark 538 is a three-dimensional landmark such as a drilled hole or an elongate guide pin, the target trajectory 434 of the landmark may bear some significance. In FIG. 7, the depicted target trajectory 434 corresponds to a desired drilling trajectory for an aperture which receives a device shaft 540 at a later stage of the surgical procedure. In this sense, therefore, at least one of the landmark guiding features 752 shown in FIG. 7 may also serve as a penetration-guiding feature.

Once the landmark(s) 538 have been virtually placed into the predetermined landmark orientation(s) at fifth action block 336 of FIG. 3 and the patient-specific template 750 created at sixth action block 342, the stock device 424 may be (virtually) re-placed upon the native patient tissue model 422 and at least one patient-specific placement guide 958 may be generated at seventh action block 356 of FIG. 3. The patient-specific placement guide 958 may be configured to interact simultaneously with at least one previously placed landmark (here, at least guide pin-type landmark 538a) and with the stock device 424 when the stock device is in the predetermined device orientation.

The patient-specific placement guide 958 may be, for example, similar to any of those disclosed in co-pending U.S. patent application No. to be determined, filed Oct. 27, 2011, titled "System and Method for Assisting with Attachment of a Stock Implant to a Patient Tissue" and claiming priority to U.S. Provisional Patent Application No. 61/408,324, filed Oct. 29, 2010 and titled "System and Method for Assisting with Attachment of a Stock Implant to a Patient Tissue", the entire contents of both of which are incorporated herein by reference, or in co-pending U.S. patent application No. to be determined, filed Oct. 27, 2011, "System and Method for Assisting with Attachment of a Stock Instrument to a Patient Tissue" and claiming priority to U.S. Provisional Patent Application No. 61/408,376, filed Oct. 29, 2010 and titled "System and Method for Assisting with Attachment of a Stock Instrument to a Patient Tissue", the entire contents of both of which are incorporated herein by reference.

Regardless of the type of patient-specific placement guide 958 provided, the patient-specific placement guide may be generated similarly to the patient-specific template 750. Namely, a placement guide blank 854, shown in FIG. 8, may be automatically or manually selected, optionally from a library of available placement guide blanks. It is contemplated that the placement guide blank 356 may be selected responsive to the selection of the stock device 424, because in many applications of the present invention, the patient-specific placement guide 958 will nest into or mate with some physical feature of the stock device. For example, and as shown in particularly the transverse view of FIG. 8, the placement guide blank 356 may nest with a portion of the stock device 424 substantially collinear with the device shaft 540 to help positively locate the patient-specific placement guide with respect to the stock device.

Figure 9:
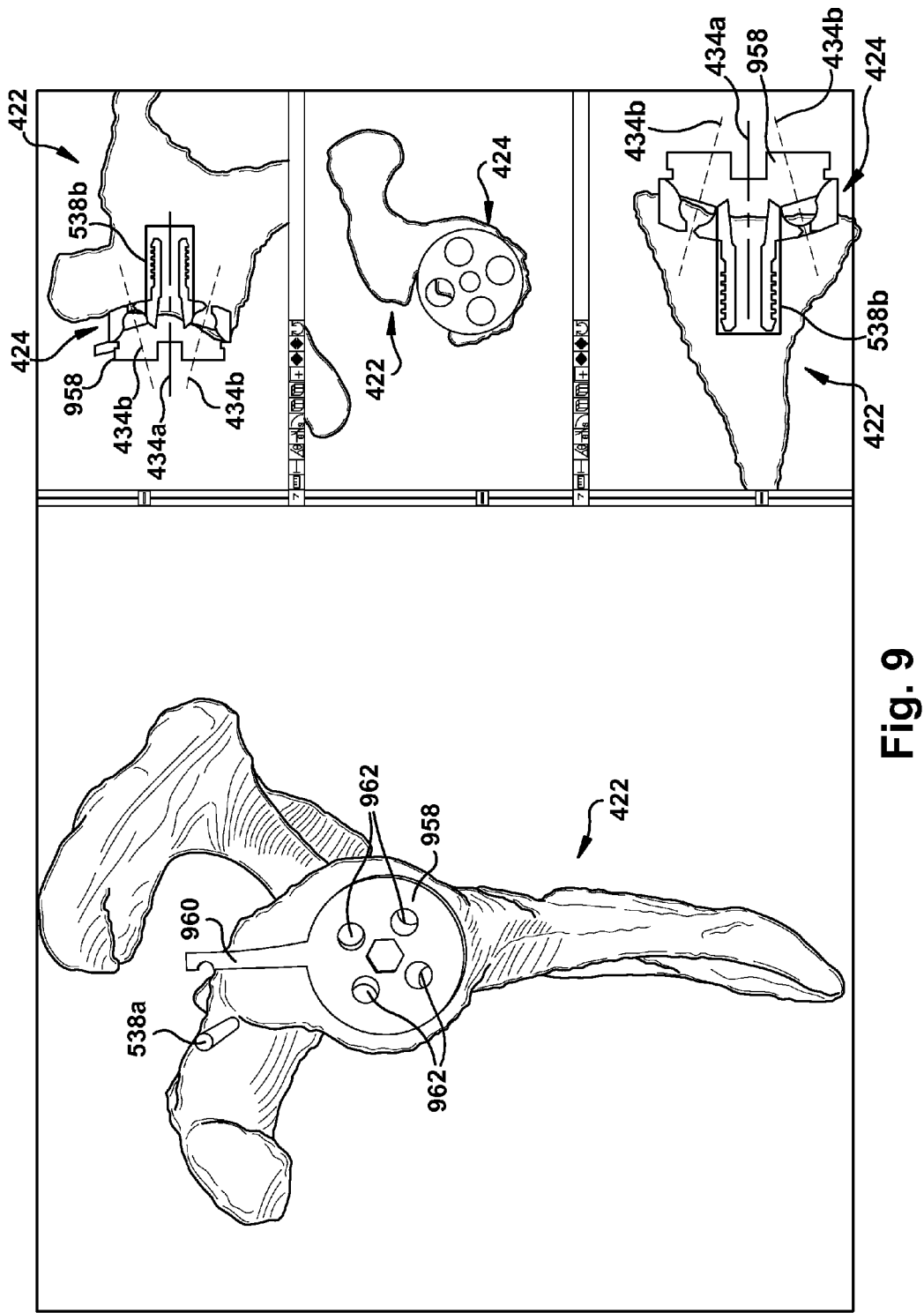

The placement guide blank 854, once selected by any suitable procedure, may then be (virtually) altered to register with at least one landmark 538, as shown in FIG. 9 when the patient-specific placement guide 958 is mated with the stock device 424 and the stock device is in the predetermined device orientation. Registration of the patient-specific placement guide 958 with a chosen landmark 538 helps to indicate that the stock device 424 has achieved the predetermined device orientation when the patient-specific placement guide 958 is mated or nested with the stock device and the stock device is in contact with the native patient tissue model. The term "register" or "registration" is used herein to indicate a predetermined condition of correct alignment or proper relative position between a landmark 538 (of any type) and some feature of the structure (here, the patient-specific placement guide 958) being registered. For example, when the landmark 538 is a two-dimensional marking on the native patient tissue model 422, the registration might occur when an inscribed mark on the patient-specific placement guide 958 aligns with the two-dimensional landmark.

As another example, and as shown in FIG. 9, the landmark 538a might be a three-dimensional landmark such as a guide pin. In this instance, the patient-specific placement guide 958 includes at least one orienting feature 960 (having previously been provided to the guide blank) which will register with the selected landmark 538a by contact with the guide pin embodying that landmark when the patient-specific placement guide 958 is mated or nested with the stock device 424 (as shown in FIG. 9) and the stock device is in contact with the native patient tissue model in the predetermined device orientation. In the view of FIG. 9, the stock device 424 is not yet in the predetermined device orientation as indicated by the separation of the orienting feature 960 and the landmark 538a, though the patient-specific placement guide 958 is mated with the stock device, as can be seen in particularly the coronal and transverse views of FIG. 9.

In addition to the guiding/orienting function provided by the patient-specific placement guide 958, at least one penetration-guiding feature 962 (four shown in FIG. 9) may be provided by the patient-specific placement guide. Here, the target trajectory 434a indicates a target trajectory and associated penetration location associated with a landmark 538b, whereas the target trajectories marked 434b (shown in dashed line in the coronal and transverse views since not strictly present in those sections) and the associated penetration locations in FIG. 9 are associated with one or more penetrating structures (not shown in FIG. 9), such as fasteners, drill bits, other surgical tools, or any other components used in the surgical procedure which the user wishes to guide with the assistance of the patient-specific placement guide 958.

FIG. 10 is similar to FIG. 9, though the stock device 424 has been reoriented into the predetermined device orientation, as indicated by the registration of the orienting feature 960 and the landmark 538a. As can also been seen in FIG. 10, the body of the patient-specific placement guide 958 has been rotated sufficiently to bring the penetration-guiding features 962 into a different rotational orientation with respect to the native patient tissue model 422 than that of FIG. 9. The target trajectories 434b of the penetration-guiding features 962 should be in the desired penetration locations with respect to the native patient tissue model 422 when the stock device 424 has been brought into the predetermined device orientation.

Once the patient-specific template 750 and/or the patient-specific placement guide 958 have been generated as desired, including any desired features as described above, a physical version of the patient-specific template is created at eighth action block 364 of FIG. 3 and a physical version of the patient-specific placement guide is created at ninth action block 366 of FIG. 3. These physical versions of the patient-specific template 750 and/or the patient-specific placement guide 958 are tangible (e.g., material and palpable) representations of the virtual versions of the corresponding items as manipulated, adjusted, and otherwise created using a system similar to that shown via the user views of FIGS. 4-10.

Optionally, and as shown in tenth action block 368 of FIG. 3, a physical three-dimensional version of the native patient tissue model 422 may be fabricated as a tangible (e.g., material and palpable) representation of the virtual version of the native patient tissue model. This physical native patient tissue model (not shown) may be useful in preoperative planning, visualization, and consideration of the surgical procedure by the user (e.g., for assisting with performing the surgery using patient specific templates and/or adjustable surgical instruments). To that end, the physical native patient tissue model may include at least one information feature providing clinically useful information to the user. "Clinically useful" information is used herein to indicate any information, other than the structure of the native patient tissue itself, that assists one of ordinary skill in the art with some pre- and/or intra-operative task. An "information feature" is any physical feature or characteristic of the physical native patient tissue model which signifies or communicates the clinically useful information to the user, optionally in combination with a preoperative plan. For example, only a portion of the scapula 100 may be fabricated as a physical native patient tissue model, with planar faces bounding the omitted portions of the scapula. Those planar faces may be chosen at predetermined distances from, and/or with predetermined orientations with respect to, a structure of interest on the physical native tissue model. As another example, an information feature may be a physical characteristic that facilitates transfer of information from the native patient tissue model 422 to the actual patient anatomy, perhaps by facilitating the setting of an adjustable, reusable tool such as that disclosed in co-pending U.S. patent application Ser. No. 12/854,362, filed Aug. 11, 2010 and titled "Method and Apparatus for Insertion of an Elongate Pin into a Surface", the entire contents of which are incorporated herein by reference.

In one example embodiment of a physical native tissue model giving spatial information, for instance, a planar face bounding a lower portion of the physical native tissue model may be substantially parallel to a transverse plane of the scapula 100. Often the patient is oriented during surgery such that the plane of the scapula 100 is not identifiable with reference to the orientation of the glenoid vault 110 in the surgical field. Accordingly, by placing the physical native tissue model with an information feature in a known position (e.g, by placing a lower face of the physical native tissue model flat on a table), one of ordinary skill in the art can readily envision obscured portions of the patient's native tissue anatomy through reference to the physical native tissue model, which may be configured to provide the user with a visualization of the native patient tissue in the same orientation as in the patient's body but without the surrounding tissue that prevents the user from directly seeing structures such as, but not limited to, the acromion process 106, the coracoid process 108, or any other structure of the scapula 100. This may be particularly useful when the physical native tissue model is fabricated at a 1:1 scale with the native patient anatomy, but also will have utility when the model is scaled up or down from the patient's actual tissue.

As another example embodiment of a physical native tissue model giving spatial information, a pin-receiving aperture may be provided in the physical native tissue model, to receive a guide pin and thus demonstrate a certain direction or axis to the user with respect to the native tissue. As a corollary to this example, an axis-, direction-, or plane-indicating structure may extend from the physical native tissue model to serve as a user visualization aid or reference.

The physical native tissue model could be used to interact with an implant or instrument before or during the surgical procedure, as well. For example, a user could rehearse certain interactions of an implant or instrument with the physical native tissue model to gain familiarity with the way that the implant or instrument is likely to intraoperatively interact with the patient's native tissue.

Physical native tissue models with information features or specific landmarks related to the preoperatively developed surgical plan are not currently provided or used as references during surgical procedures. The availability of a physical native tissue model to use as a reference in this manner may supplement or even supplant the need for intraoperative imaging, which is likely to reduce cost, operating room clutter, and time required for the surgical procedure.

The patient's name, identification number, surgeon's name, and/or any other desired identifier may be molded into, printed on, attached to, or otherwise associated with the physical version(s) of the patient-specific template 750, the patient-specific placement guide 958, and/or the native patient tissue model 422 in a legible manner. The tangible representations of the patient-specific template 750, the patient-specific placement guide 958, and/or the native patient tissue model 422 may be made by any suitable method such as, but not limited to, selective laser sintering ("SLS"), fused deposition modeling ("FDM"), stereolithography ("SLA"), laminated object manufacturing ("LOM"), electron beam melting ("EBM"), 3-dimensional printing ("3DP"), contour milling from a suitable material, computer numeric control ("CNC"), other rapid prototyping methods, or any other desired manufacturing process.

Once the physical versions of the patient-specific template 750, the patient-specific placement guide 958, and/or the native patient tissue model 422 have been manufactured and prepared for use (e.g., mechanically or chemically cleaned, cured, sterilized, or the like) using any suitable process(es), they are available for use during surgical procedures as described above and in the incorporated references.

The preoperative planning system disclosed herein allows the user to experiment with different placements and selections of stock devices 424 and/or custom or patient-specific components in an effort to produce positive patient outcomes. FIGS. 11A-14B depict various examples of steps, alternate options, and considerations that one of ordinary skill in the art may find useful in preoperative planning, particularly with respect to selection of the stock device 424 and of the predetermined device orientation.

Figure 11B:
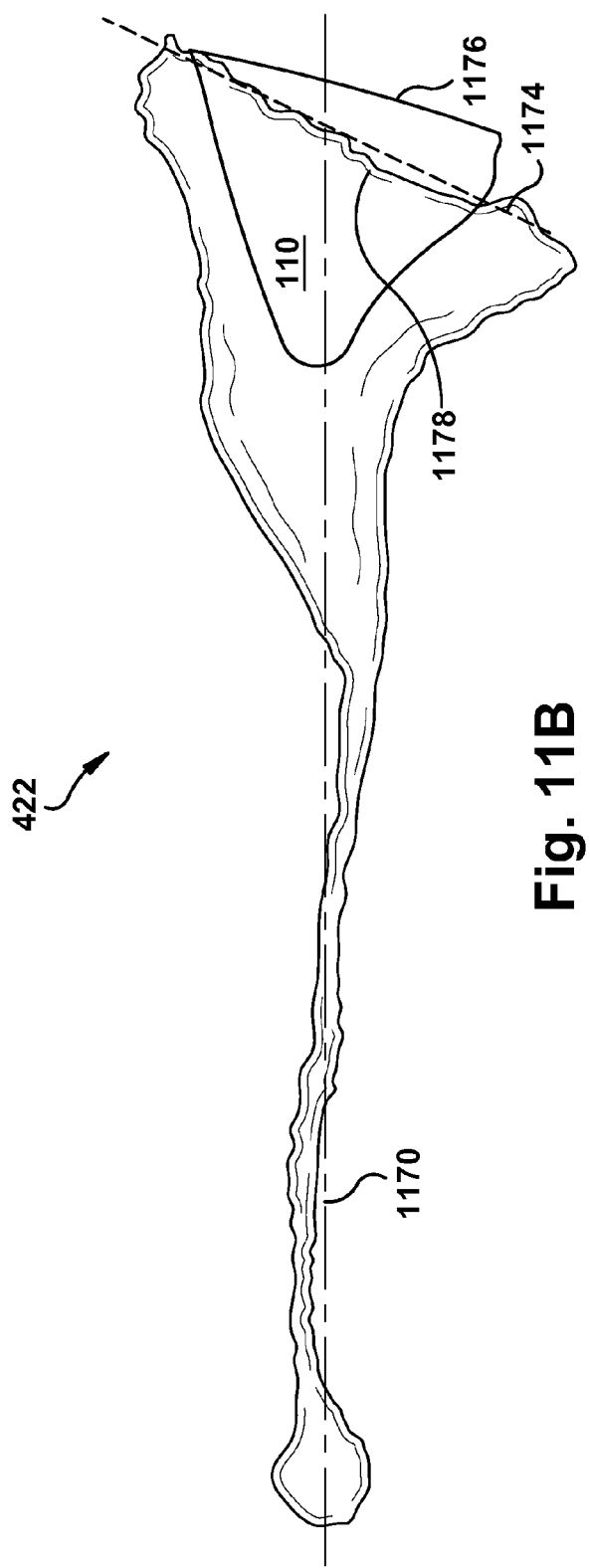

FIGS. 11A-11B depict a transverse view of a native patient tissue model 422 of a typical clinical case of a patient with osteoarthritis, having moderate bone loss. The scapular plane 1170 is perpendicular to reference plane 1172. The reference plane also represents the 0.degree. reference from which glenoid version is measured. The lower portion of FIGS. 11A-11B is posterior and the top portion of these Figures is anterior, as shown by direction arrow 118'. The diagonal dashed line labeled 1174 represents the native glenoid plane of the patient. In this case, the native glenoid plane 1174 exhibits a retroversion angle of approximately 26.degree. from the reference plane 1172. Glenoid version in the normal population is reported to commonly be between 5.degree. of anteversion and 15.degree. of retroversion. The average normal glenoid version is approximately 1-2.degree. of retroversion.

The goal of arthroplasty surgery is to correct pathologic anatomy and restore as best as possible normal anatomy and function. Corrective options range between placing an implant component at the standard ideal of perpendicular to the plane of the scapula (0.degree.) up to the pathologic version (in this case, 26.degree. of retroversion). Common practice today is to correct version with an attempt to place a stock device 424 approximately perpendicular to the scapular plane 1170 (i.e., lying along the reference plane 1172 at about 0.degree. of version). For clarity of description, the "angle" of the stock device 424 is referenced hereafter as being the angle measured from a top face of the stock device, the top face being foremost in the perspective view of FIG. 4.

There normally will be a secondary surgical goals to minimize removal of patient tissue needed to accommodate the stock device 424, seat the entire stock device on the prepared patient tissue surface, and minimize unwanted perforation of the outer walls of the glenoid vault 110 or other patient tissue by the device shaft 540 or another penetrating structure 430 used in the surgical procedure or remaining in the patient tissue postoperatively. When formulating a preoperative plan, typical items of concern include the bone (or other patient tissue) loss in the patient, the position and orientation of the normal joint line, and where the stock device 424 or other component should be placed to aim toward a positive patient outcome.

The present inventors have found that an average patient tissue model 1176 (e.g., a "vault model") may be useful in tailoring a surgical procedure to fit the needs of an individual patient. A suitable average patient tissue model 1176 is described in co-pending U.S. patent application Ser. No. 12/043,634, filed Mar. 6, 2008, and titled "Method and Apparatus for Preparing for a Surgical Procedure", the contents of which are hereby incorporated by reference in their entirety. In a similar manner, the shape of an average acetabular vault may be used as a suitable average patient tissue model and have some clinical relevance when defining the normal anatomic relationships from the pathologic anatomy in a hip use environment. The average patient tissue model 1176 of a glenoid vault 110 is shown superimposed on the native patient tissue model 422 in FIG. 11B. Although this is an "average" view, the contours of the average patient tissue model 1176 can be seen to substantially mirror the contours of the native glenoid vault 110 of even the depicted pathologic scapula 100.

FIG. 11B is similar to FIG. 11A, with the addition of an average patient tissue model 1176. The average patient tissue model 1176 helps to define the location of the normal joint line and the version of the normal glenoid fossa 1178 in a patient-specific manner. The average patient tissue model 1176 may help define reconstruction goals in pathologic cases, and may assist with selection of position and type of a stock device 424 or a custom device (not shown). Selection of version for the stock device 424 may be at least partially dependent upon the version of the average patient tissue model 1176 which defines patient-specific normal anatomy. In the patient of FIGS. 11A-14B, normal patient version, based upon the average patient tissue model 1176, may be seen to be approximately 12.degree. of retroversion, as shown by the angle of the rightmost face (in the orientation of the Figures) of the average patient tissue model 1176 with respect to reference plane 1172.

When planning a surgical procedure using preoperative imaging, the user may specify at least one structural change to the native patient tissue to facilitate placement of a stock device in a predetermined device orientation. For example, native patient tissue could be drilled, planed, reamed or otherwise removed, or the native patient tissue could be built up using bone grafts or other substances, with the latter being much more difficult to do than the former during a standard surgical procedure. Using the system described above, a (virtual) altered patient tissue model (not shown) can be generated and viewed or otherwise used in the preoperative planning. Optionally, a physical three-dimensional version of the altered patient tissue model may be fabricated as a tangible representation of the virtual version of the altered patient tissue model. When provided, the physical altered patient tissue model may also include at least one information feature providing clinically useful information to the user. For example, a landmark 538 (e.g., a cavity or aperture) may be present in the physical altered patient tissue model and may therefore be made palpable to the user during the surgical procedure. The physical altered patient tissue model, when present, may be used and referenced similarly to the aforementioned physical native patient tissue model.

FIGS. 12A-14B are partial transverse cross-sectional schematic views of a scapula which depict a comparison of the likely surgical outcomes for various preoperative planning options. FIGS. 12A-14B depict various ways in which the native patient tissue model 422 can be compared to a reference patient tissue model (regardless of whether any alterations are made to the native patient tissue model), and the effect of that comparison on the predetermined device orientation. The predetermined device orientation can be adjusted, automatically by the system and/or manually by the user, responsive to the comparison of the native patient tissue model 422 to the reference patient tissue model. The reference patient tissue may be at least one of a (mirrored) image of a contralateral patient tissue of the same or a different patient, a value taken from a standard reference patient tissue, a value range taken from a standard reference patient tissue, and the aforementioned average patient tissue model 1176. In FIGS. 12A-14B, the reference patient tissue is shown and described as being the average patient tissue model 1176. In FIG. 12A, a stock device 424 has been superimposed upon the native patient tissue model 422 of FIGS. 11A-11B in a version of 0.degree. from the coronal plane (shown in FIGS. 11A-13C as scapular plane 1170), with the bottom portion (in the orientation of FIGS. 11A-13C) of the stock device being located on an outer surface of the native patient tissue. Since FIGS. 12A-13C show the scapula 100 having portions of the native tissue removed to accommodate each stock device 424, the patient tissue shown can be described as an altered patient tissue model 1280. The excision of fairly large amounts of native patient tissue is likely to adversely affect the dynamics within the shoulder joint. Additionally, the glenoid vault 110 may be shaved down enough that the device shaft 540 is in danger of breaching the glenoid vault wall, which is generally undesirable and can cause patient discomfort and possibly result in undesirable reoperation. Accordingly, one goal of a pre-surgical planning process using the average patient tissue model 1176 is to attempt to replicate the total volume (or area, as depicted in the cross-sectional views of FIGS. 12A-14B) of the average patient tissue model 1176 with a combination of the total volume (or area) of the altered patient tissue model 1280 and the stock device 424.

It is apparent from FIG. 12A that a substantial amount of the native patient tissue will have to be removed from the native patient tissue model 422 to allow the stock device 424 to seat firmly and maintain the 0.degree. version with the stock device 424 substantially centered, posteriorly to anteriorly, upon the glenoid fossa 1178. The device shaft 540 in FIG. 12A is in danger of breaching the glenoid vault 110 wall, which should be avoided.

FIG. 12B also shows an altered patient tissue model 1280 with a relatively large volume of native patient tissue removed, though less removed than in FIG. 12A. In FIG. 12B, the version is still corrected to 0.degree. from the reference plane 1172, but the stock device 424 has been moved upward (in the orientation of the Figures) to distance the device shaft 540 from the glenoid vault 110 wall. This shifting of the stock device 424 can be seen to have a different adverse effect, however—namely, the stock device now substantially overhangs the anterior edge of the glenoid fossa 1178.

This problematic 0.degree. version correction is an example of a value taken from a standard reference patient tissue—many users will routinely correct version in all such cases to 0.degree. as shown. As an example of a value range taken from a standard reference patient tissue, the version may be corrected to a value taken from the range of −5.degree. to +5.degree., with the user's experience and intuition leading to the selection of one value from that range. Another example, in a hip standard reference patient tissue, might prescribe a range of 10-30.degree. of anteversion and 30-55.degree. of abduction for an acetabular prosthetic implantation. However, a seemingly reasonable value based upon a standard reference patient tissue—whether for a shoulder, hip, or any other type of surgery—may markedly depart from a value which leads to an acceptable result for a particular patient.

As a result, users will sometimes employ a mirror image of a contralateral native patient tissue (from that patient or another patient) to use as a reference patient tissue. However, even if there is a contralateral native patient tissue to consult (e.g., the patient is not an amputee in that respect), the contralateral native patient tissue may be pathologically or congenitally asymmetrical from even the original state of the native patient tissue which is being surgically corrected. Thus, there is a need for another reference patient tissue for comparison to the native patient tissue model 422.

In the aforementioned co-pending "Method and Apparatus for Preparing for a Surgical Procedure" U.S. patent application, the average patient tissue model 1176 (i.e., the "vault model") is proposed as providing an appropriate reference patient tissue for a wide range of patients. The average patient tissue model 1176 is shown in FIGS. 12A-13C superimposed over the altered patient tissue model 1280. Accordingly, one of ordinary skill in the art, with reference to the average patient tissue model 1176, will be motivated to preserve more of the native patient tissue by altering the native tissue model 422, and placing the stock device 424 with reference to the average patient tissue model 1176.

In the situation of FIG. 12C, the average patient tissue model 1176 helps define the native patient joint line and the native version for that particular patient. Accordingly, the average patient tissue model 1176 helps direct the selection of the stock device 424 to restore the native joint line and the patient's native version, thereby reducing the risk of excessive bone removal or perforation of the native patient tissue during or after the stock device is installed. FIG. 12C depicts an altered patient tissue model 1280 with the average patient tissue model 1176 superposed thereupon and the stock device 424 placed according to the average patient tissue model (here, rotated clockwise, in the orientation of the Figures). It can be seen that placement of the stock device 424 in a patient-specific version (informed by the average patient tissue model 1176) will center the device shaft 420 (posteriorly to anteriorly) in the glenoid vault 110, provide more thorough patient tissue contact for the stock device, and result in less patient tissue removal and greater centering of the stock device on the glenoid fossa 1178 as compared to the 0.degree. versions of FIGS. 12A and 12B. Accordingly, the stock device 424 placement in FIG. 12C would seem to provide a preferred predetermined device orientation compared to the orientations shown in FIGS. 12A and 12B.

FIGS. 13A-13C depict a similar orientation comparison sequence to that of FIGS. 12A-12C, but including a different stock device 424a than that shown in FIGS. 12A-12C. The stock device 424a includes a thickened leftmost section (in the orientation of the Figures) which helps to compensate for the pathologic state of the native patient tissue. This selection of this stock device 424a, having a second configuration as compared to the first configuration of the stock device 424 of FIGS. 12A-12C allows for the combination of the native glenoid vault 110 plus the stock device 424a to have a similar, and similarly arranged, volume of material as that of the average patient tissue model 1176. The arrangements of FIGS. 13A-13C are analogous to those of FIGS. 12A-12C, excepting the differences in the stock devices 424 and 424a, and therefore the description of FIGS. 12A-12C will not be repeated with respect to 13A-130.

The views of the combination of the altered glenoid vault 110 plus the stock device 424a of FIGS. 13A-13C may be favorably contrasted with the analogous views of FIGS. 12A-12C, wherein the combination of the altered glenoid vault 110 plus the stock device 424 has a substantially smaller volume in the latter when compared to the average patient tissue model 1176, and thus the latter will have less strength and ability to mechanically perform for the patient as needed for a suitably long time after the surgical procedure. Accordingly, the stock device 424a selection and placement of FIG. 13C appears to meet the goal of preserving native tissue the best of all of the options shown in FIGS. 12A-13C.

Figure 14B:
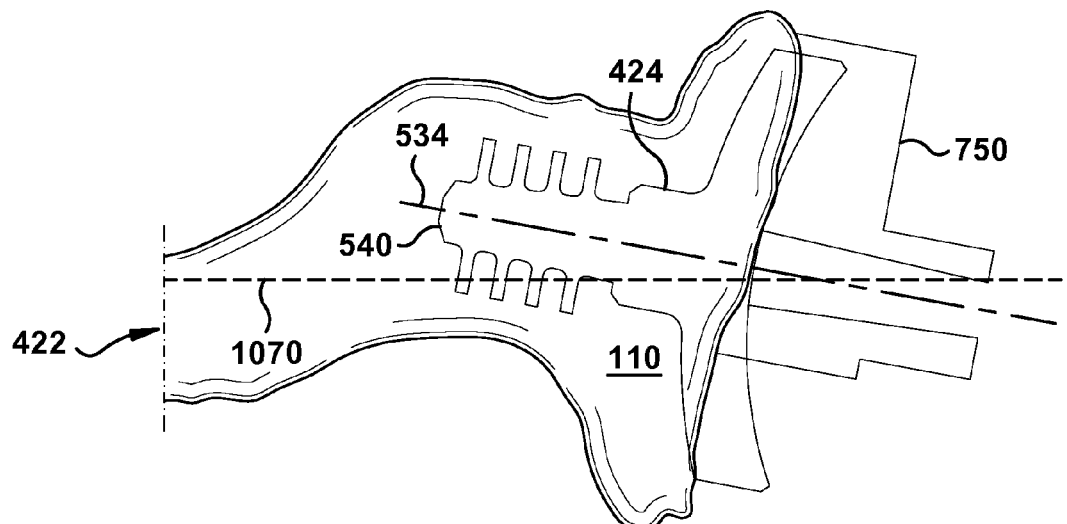
FIGS. 14A-14B are schematic views depicting options for one element of the embodiment of FIG. 3 in the first configuration.
Figure 14A:
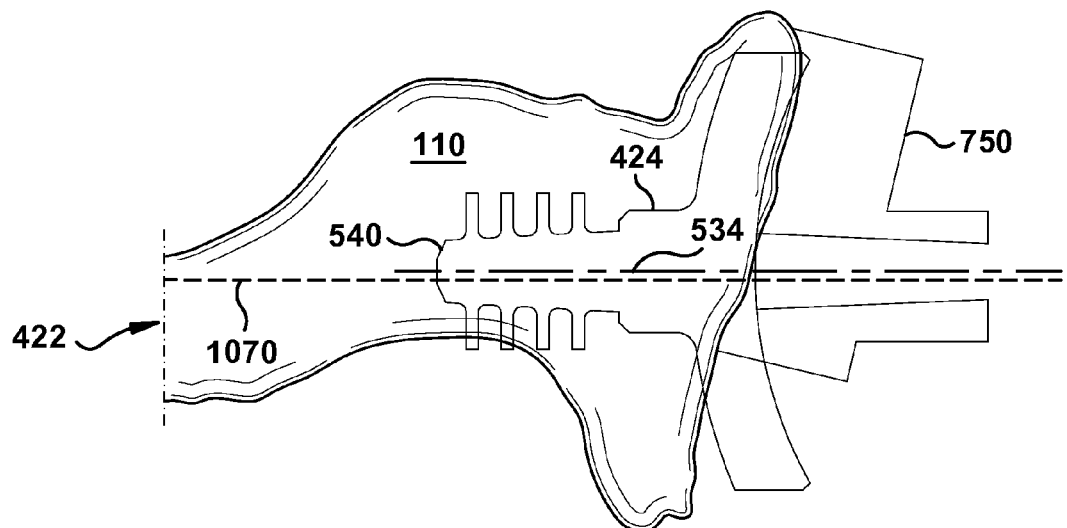

FIGS. 14A-14B show the effects of device orientation upon the native patient tissue model 422. In FIG. 14A, the version has been corrected to 0.degree. That is, the target trajectory 534 of the patient-specific template 750 is substantially parallel to the scapular plane 1170. As is apparent in FIG. 14A, the device shaft 540 is cutting markedly into the coronal bone of the scapula 100 in an undesirable manner, and a relatively large volume of native patient tissue will need to be removed (near the top of FIG. 14A) to accept the stock device 424. In FIG. 14B, the version has been corrected to a value chosen by the user with consideration of the native patient tissue model 422—the version in FIG. 14B is approximately 12.degree. As can be seen, by simply tilting the stock device 424 in FIG. 14B as suggested by the average patient tissue model 1176 or by a chosen value out of a value range taken from a standard reference patient tissue, the stock device 424 is seated more securely in the glenoid vault 110, with less removal of native patient tissue required.

Figure 15:
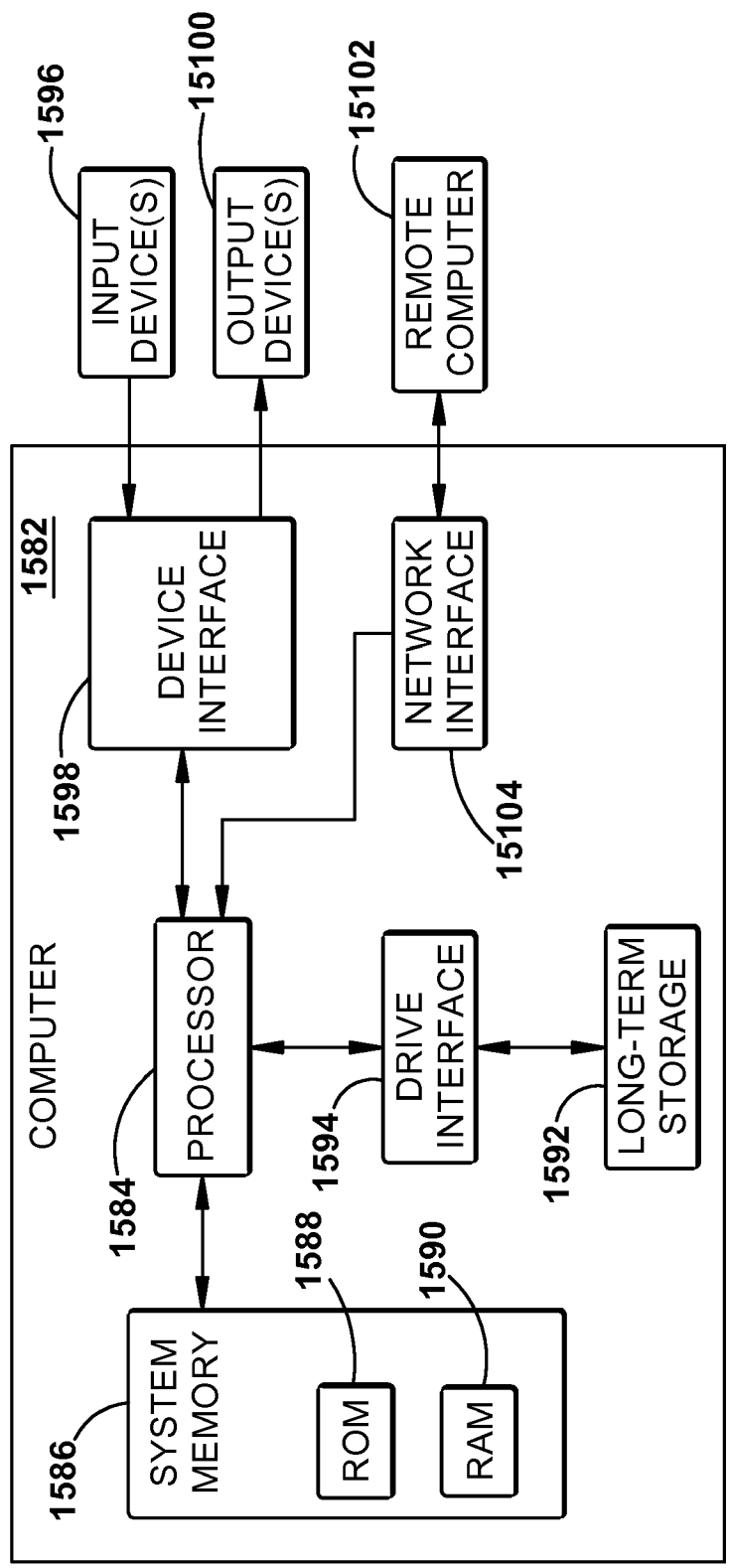
FIG. 15 is a schematic view of a computer system that can be employed to implement systems and methods described herein, such as based on computer executable instructions running on the computer system.

FIG. 15 illustrates a computer system 1582 that can be employed to implement systems and methods described herein, such as based on computer executable instructions running on the computer system. The user may be permitted to preoperatively simulate the planned surgical procedure using the computer system 1582 as desired. The computer system 1582 can be implemented on one or more general purpose networked computer systems, embedded computer systems, routers, switches, server devices, client devices, various intermediate devices/nodes and/or stand alone computer systems. Additionally, the computer system 1582 can be implemented as part of the computer-aided engineering (CAE) tool running computer executable instructions to perform a method as described herein.

The computer system 1582 includes a processor 1584 and a system memory 1586. Dual microprocessors and other multi-processor architectures can also be utilized as the processor 1584. The processor 1584 and system memory 1586 can be coupled by any of several types of bus structures, including a memory bus or memory controller, a peripheral bus, and a local bus using any of a variety of bus architectures. The system memory 1586 includes read only memory (ROM) 1588 and random access memory (RAM) 1590. A basic input/output system (BIOS) can reside in the ROM 1588, generally containing the basic routines that help to transfer information between elements within the computer system 1582, such as a reset or power-up.

The computer system 1582 can include one or more types of long-term data storage 1592, including a hard disk drive, a magnetic disk drive, (e.g., to read from or write to a removable disk), and an optical disk drive, (e.g., for reading a CD-ROM or DVD disk or to read from or write to other optical media). The long-term data storage 1592 can be connected to the processor 1584 by a drive interface 1594. The long-term data storage 1592 components provide non-volatile storage of data, data structures, and computer-executable instructions for the computer system 1582. A number of program modules may also be stored in one or more of the drives as well as in the RAM 1590, including an operating system, one or more application programs, other program modules, and program data.

A user may enter commands and information into the computer system 1582 through one or more input devices 1596, such as a keyboard or a pointing device (e.g., a mouse). These and other input devices are often connected to the processor 1584 through a device interface 1598. For example, the input devices can be connected to the system bus by one or more a parallel port, a serial port or a universal serial bus (USB). One or more output device(s) 15100, such as a visual display device or printer, can also be connected to the processor 1584 via the device interface 1598.

The computer system 1582 may operate in a networked environment using logical connections (e.g., a local area network (LAN) or wide area network (WAN) to one or more remote computers 15102. A given remote computer 15102 may be a workstation, a computer system, a router, a peer device or other common network node, and typically includes many or all of the elements described relative to the computer system 1582. The computer system 1582 can communicate with the remote computers 15102 via a network interface 15104, such as a wired or wireless network interface card or modem. In a networked environment, application programs and program data depicted relative to the computer system 1582, or portions thereof, may be stored in memory associated with the remote computers 15102.

It is contemplated that multiple versions of the patient-specific template 750 and/or the patient-specific placement guide 958 could be created during preoperative planning and fabricated as options for the user to select from during the surgical procedure. For example, the user may not be able to clear away surrounding (e.g., soft) tissue from the native patient tissue as well as expected. In this situation, it may be useful to have a patient-specific template 750 with a smaller footprint for easier insertion into the surgical wound and manipulation at the surgical site, even though the smaller footprint means that there is less mating surface 748 to mate with the native patient tissue and provide positive location assistance for the patient-specific template 750.

While aspects of the present invention have been particularly shown and described with reference to the preferred embodiment above, it will be understood by those of ordinary skill in the art that various additional embodiments may be contemplated without departing from the spirit and scope of the present invention. For example, the specific methods described above for using the described system are merely illustrative; one of ordinary skill in the art could readily determine any number of tools, sequences of steps, or other means/options for virtually or actually placing the above-described apparatus, or components thereof, into positions substantially similar to those shown and described herein. Any of the described structures and components could be integrally formed as a single piece or made up of separate sub-components, with either of these formations involving any suitable stock or bespoke components and/or any suitable material or combinations of materials; however, the chosen material(s) should be biocompatible for most applications of the present invention. The mating relationships formed between the described structures need not keep the entirety of each of the "mating" surfaces in direct contact with each other but could include spacers or holdaways for partial direct contact, a liner or other intermediate member for indirect contact, or could even be approximated with intervening space remaining therebetween and no contact. Though certain components described herein are shown as having specific geometric shapes, all structures of the present invention may have any suitable shapes, sizes, configurations, relative relationships, cross-sectional areas, or any other physical characteristics as desirable for a particular application of the present invention. An adhesive (such as, but not limited to, bone cement) could be used in conjunction with the system and method described herein. The patient-specific template 750 and/or the patient-specific placement guide 958 may include a plurality of structures cooperatively forming the base body and temporarily or permanently attached together in such a manner as to permit relative motion (e.g., pivoting, sliding, or any other motion) therebetween. The patient-specific placement guide 958 may not actually be patient-specific but could instead be a stock item in situations where the landmark(s) 538 are placed to "standardize" a particular native patient tissue model with a standard frame of reference. Any structures or features described with reference to one embodiment or configuration of the present invention could be provided, singly or in combination with other structures or features, to any other embodiment or configuration, as it would be impractical to describe each of the embodiments and configurations discussed herein as having all of the options discussed with respect to all of the other embodiments and configurations. Any of the components described herein could have a surface treatment (e.g., texturization, notching, etc.), material choice, and/or other characteristic chosen to provide the component with a desired interaction property (e.g., tissue ingrowth, eluting of a therapeutic material, etc.) with the surrounding tissue. The system is described herein as being used to plan and/or simulate a surgical procedure of implanting one or more prosthetic structures into a patient's body, but also or instead could be used to plan and/or simulate any surgical procedure, regardless of whether a non-native component is left in the patient's body after the procedure. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

The invention claimed is:

1. A method of preoperative planning, the method comprising:
    creating a virtual model of a native patient tissue;
    placing a virtual device into a desired device orientation relative to the virtual model of the native patient tissue;
    specifying at last one structural change to the virtual model of the native patient tissue to facilitate placement of the virtual device in the desired device orientation, the at last one structural change based on removing tissue from the virtual model of the native patient tissue or adding tissue to the virtual model of the native patient tissue;
    creating a virtual model of at least one patient-specific template, the at least one patient-specific template configured to mate with the virtual model of the native patient tissue, the at last one patient-specific template including a landmark guiding feature configured to direct at last one virtual non-tissue landmark at a predetermined orientation when the patient-specific template is mated with the virtual model of the native patient tissue;
    creating a virtual model of an altered patient tissue responsive to specifying the at least one structural change to the native patient tissue; and
    fabricating a tangible representation of a bone using the virtual model of the altered patient tissue.

2. The method according to claim 1, wherein fabricating the tangible representation of the bone includes fabricating the tangible representation using one of selective laser sintering, fused deposition modeling, stereolithography, laminated object manufacturing, electron beam melting, 3-dimensional printing, contour milling, computer numeric control fabricating.

3. The method according to claim 1, further comprising providing the tangible representation of the bone with a tangible version of the virtual device.

4. The method according to claim 3, wherein providing the tangible version of the virtual device comprises providing an implant.

5. The method according to claim 1, wherein specifying the at least one structural change to the native patient tissue includes comparing the native patient tissue with a reference patient tissue model, the reference patient tissue model being at least one of a contralateral patient tissue model, a standard reference patient tissue value, a standard reference patient tissue value range, and a predetermined average patient tissue model.

6. The method of claim 1, wherein fabricating the tangible representation of the bone comprises including at least one information feature providing clinically useful information for a user.

7. The method of claim 1, wherein placing the virtual device into the desired device orientation comprises choosing at least one device property, the at least one device property including at least one of device size, device shape, device material, number of fasteners, type of fasteners, size of fasteners, shape of fasteners, amount of patient tissue alteration, type of patient tissue alteration, and physical quality of the native patient tissue.

8. The method of claim 1, further comprising choosing the virtual device from a library of available virtual devices.

9. The method of claim 1, further comprising:
virtually placing at least one non-tissue landmark in a predetermined landmark orientation with respect to the desired device orientation;
virtually modeling at least one patient-specific template, the at least one patient-specific template being configured to mate with the native patient tissue and with the virtual device, the patient-specific template having a landmark guiding feature configured to place the non-tissue landmark in the predetermined landmark orientation when the patient-specific template is mated with the native patient tissue and with the virtual device; and
creating a tangible version of the at least one patient-specific template.

10. The method according to claim 1, wherein the native patient tissue comprises the bone.

11. The method according to claim 1, wherein the virtual device is an implant.

12. The method according to claim 1, wherein the tangible representation of the bone comprises a representation of patient tissue configured to receive the virtual device.

13. The method according to claim 12, wherein the virtual device comprises an implant.

14. The method according to claim 1, wherein the tangible representation of the bone differs from the bone in that the tangible representation of the bone is free of a portion corresponding to tissue to be removed from the bone to accommodate the virtual device.

15. The method according to claim 1, wherein the tangible representation of the bone differs from the bone in that the tangible representation of the bone includes a portion corresponding to tissue to be added from the bone to accommodate the virtual device.

16. The method according to claim 1, wherein the tangible representation of the bone comprises a surface of a bone configured to receive the virtual device.

17. The method of claim 1, wherein specifying at least one structural change to the virtual model of the native patient tissue is based on the placement of the virtual device into the desired device orientation relative to the virtual model of the native patient tissue.

18. A method comprising:
creating a virtual model of a native patient tissue;
placing a virtual device into a desired device orientation relative to the virtual model of the native patient tissue;
specifying at least one structural change to the virtual model of the native patient tissue to facilitate placement of the virtual device in the desired device orientation, the at last one structural change based on removing tissue from the virtual model of the native patient tissue;
creating a virtual model of at last one patient-specific template, the at last one patient-specific template configured to mate with the virtual model of the native patient tissue, the at least one patient-specific template including a landmark guiding feature configured to direct at least one virtual non-tissue landmark at a predetermined orientation when the patient-specific template is mated with the virtual model of the native patient tissue;
creating a virtual model of an altered patient tissue responsive to specifying the at last one structural change to the native patient tissue; and
fabricating a tangible representation of a bone using the virtual model of the altered patient tissue.

19. The method of claim 18, further comprising:
placing at least one virtual non-tissue landmark in a predetermined landmark orientation with respect to the desired device orientation; and
wherein:
the at least one patient-specific template is configured to guide a penetrating structure toward the virtual model of the native patient tissue; and
the virtual model of the altered patient tissue is based on the virtual model of the at least one patient-specific template.

* * * * *